United States Patent [19]

Nakano et al.

[11] Patent Number: 4,652,566
[45] Date of Patent: Mar. 24, 1987

[54] BENZOFURAN DERIVATIVES, PROCESSES FOR PREPARING THE SAME AND ANTIHYPERTENSIVE AGENTS CONTAINING THE SAME

[75] Inventors: Jun Nakano, Moriyama; Michiko Nagahara, Shiga; Mitsuo Hayashida, Kusatsu; Yuji Suzuki, Otsu; Yohichi Maruyama, Shiga, all of Japan

[73] Assignee: Kaken Pharmaceutical Co., Ltd., Tokyo, Japan

[21] Appl. No.: 713,662

[22] Filed: Mar. 19, 1985

[30] Foreign Application Priority Data

Mar. 27, 1984 [JP] Japan .................................. 59-60399

[51] Int. Cl.$^4$ .................. A61K 31/395; C07D 405/12
[52] U.S. Cl. ..................................... 514/253; 544/376
[58] Field of Search .......................... 544/376; 514/253

[56] References Cited

U.S. PATENT DOCUMENTS 4,234,726 11/1980 Gardner ............................. 544/376

Primary Examiner—Robert T. Bond
Attorney, Agent, or Firm—Armstrong, Nikaido, Marmelstein & Kubovcik

[57] ABSTRACT

A [2-hydroxy-3-(4-phenylpiperazinyl)propoxy]benzofuran derivative having the formula (I):

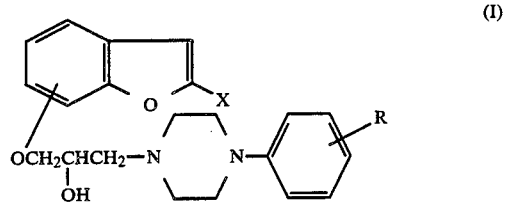

wherein X is acetyl, carbamoyl, cyano, a lower alkoxycarbonyl, carboxyl or 1-hydroxyethyl group, R is hydrogen atom, a lower alkoxy group, a lower alkyl group or a halogen atom; R is attached to an arbitrary position of ortho-position, meta-position and para-position to N-phenyl group, and a group having the formula:

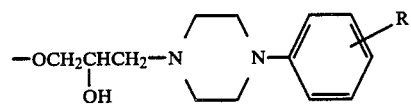

is attached to an arbitrary position of 4, 5, 6 and 7 positions to benzofuran ring or the salt thereof, a process for preparing the same and an antihypertensive agent containing the same as an effective component. The benzofuran derivative has a strong α-adrenergic blockade effect and calcium antagonistic effect with a more decreased side-effect.

33 Claims, No Drawings

BENZOFURAN DERIVATIVES, PROCESSES FOR PREPARING THE SAME AND ANTIHYPERTENSIVE AGENTS CONTAINING THE SAME

BACKGROUND OF THE INVENTION

The present invention relates to [2-hydroxy-3-(4-phenylpiperazinyl)propoxy]benzofuran derivatives which hitherto have never been described in any literature, processes for preparing the same and antihypertensive agents containing the same as an effective component.

Various cardiovascular agents having a benzofuran ring have been already developed. However, antihypertensives having plural pharmacological efficiencies such as an α-adrenergic blockade effect and a calcium antagonistic effect as well as a β-adrenergic blockade effect, and moreover a decreased side-effect have never been obtained.

As a result of the inventor's continuous studies aiming at an antagomistic agent which functions at a level of the receptor of sympathetic nervous system, [2-hydroxy-3-(4-phenylpiperazinyl)propoxy]benzofuran derivatives, i.e. new compounds which have a strong α-adrenergic blockade effect and calcium antagonistic effect with a more decreased side-effect are found and the present invention is accomplished.

SUMMARY OF THE INVENTION

Namely, the present invention relates to [2-hydroxy-3-(4-phenylpiperazinyl)propoxy]benzofuran derivatives having the formula (I):

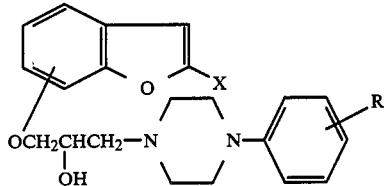

(I)

wherein X stands for acetyl, carbamoyl, cyano, a lower alkoxycarbonyl, carboxyl or 1-hydroxyethyl group and R is selected from hydrogen atom, a lower alkoxy group, a lower alkyl group or a halogen atom; R is substituted arbitrarily at ortho-position (hereinafter referred to as "O-position"); meta-position (hereinafter referred to as "m-position") or para-position (hereinafter referred to as "p-position") to N-phenyl group and the group having the formula:

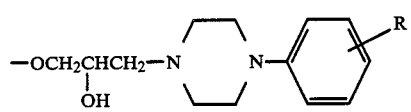

is substituted arbitrarily at 4, 5, 6 or 7 position of benzofuran ring or the salts thereof, a process for preparing the same and antihypertensive agents containing the same as an effective component.

DETAILED DESCRIPTION

In the present invention, the term "lower" means a linear or a branched carbon chaim having 1 to 3 carbon atoms. Therefore, in case that R is a lower alkyl group, R is selected from methyl, ethyl, n-propyl or isopropyl group, preferably methyl group. In case that R is a lower alkoxy group, R is selected from methoxy, ethoxy, n-propoxy or isopropoxy group, preferably, methoxy gorup. In case that R is a halogen atom, R is selected from fluorine, chlorine or bromine atom, preferably chlorine atom.

Besides, R may be substituted at any position of o-position, m-position or p-position to N-phenyl group, preferably, at o-position.

The substituent group attached to the benzofuran ring, which has the formula:

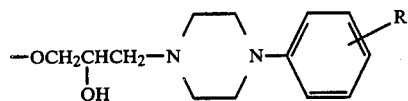

may be substituted at any of 4, 5, 6 or 7 position, preferably 5 or 7 position.

Examples of the substituent group X are, for instance, acetyl, carbamoyl, cyano, a lower alkoxycabonyl, carboxyl, 1-hydroxyethyl, and the like. In case that X is 1-hydroxyethyl group or carboxyl group in the compound (I), the compound is also an active metabolite produced from the compound (I) in which X is acetyl or carbamoyl group in a living body.

The salts of the [2-hydroxy-3-(4-phenylpiperazinyl)propoxy]benzofuran derivatives are the salts of mineral acids or of organic acids which are pharmacologically acceptable. Examples of such salt are, for instance, hydrochloride, sulfate, nitrate, acetate, oxalate, tartrate, citrate, lactate, and the like.

Besides, [2-hydroxy-3-(4-phenylpiperazinyl)propoxy]benzofuran derivatives of the present invention includes all optically active isomers and mixture thereof since they have at least one asymmetric carbon atom, in case that X is 1-hydroxyethyl group, they have two asymmetric carbon atoms.

In the present invention, the compound (I) can be prepared by the four kinds of process as follows.

[The process 1]

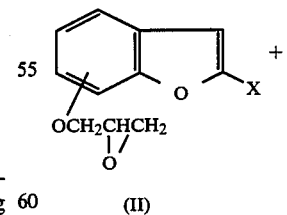

(II)

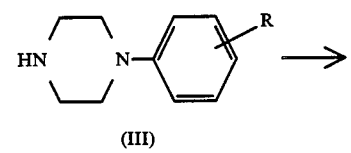

(III)

-continued
[The process 1]

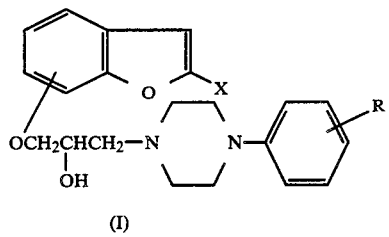

wherein X and R are the same as above. This is the process for preparing the compound (I), characterized in that [2,3-epoxypropoxy]benzofuran derivatives (II) is added with N-phenylpiperazine derivatives (III) or the salt thereof.

The above-mentioned reaction is generally carried out by subjecting an equimolar to 1.5 times molar amount of the compound (III) as compared with the compound (II) to the compound (II) in an organic solvent. In the above reaction, an equimolar to 1.5 tiems molar amount of base as compared with the compound (II), such as sodium hydroxide, potassium hydroxide, sodium carbonate, potassium carbonate, trimethylamine and triethylamine, is added to the reaction system when the compound (III) is employed as the acid addition salt. The examples of the employed organic solvent are, for instance, methanol, ethanol, 2-propanol, acetonitrile, tetrahydrofuran, dioxane, dimethoxyethane, dimethylformamide, and the like.

The reaction temperature and the reaction time are not particularly limited. In general, the reaction is carried out at room temperature to about 100° C. for about 15 minutes to about 10 hours.

The separation and the purification of the compound (I) may be carried out by means of a conventional procedure such as solvent extraction, separation by chromatography and crystallization.

In the above-mentioned reaction of the process, [2,3-epoxypropoxy]benzofuran derivatives (II) are the novel compounds which have never been described in any literature when X is carbamoyl, cyano, a lower alkoxy carbonyl or carboxyl group. In case that X is acetyl group, see Japanese Examined Patent Publication (KOKOKU) No. 20063/1975. In case that X is 1-hydroxyethyl group, see Japanese Unexamined Patent Publication (KOKAI) No. 89665/1977.

The novel [2,3-epoxypropoxy]benzofuran derivatives (II) except for a case that X is carboxyl group can be obtained from epichlorohydrin and hydroxybenzofuran derivative (IX) having the formula (IX):

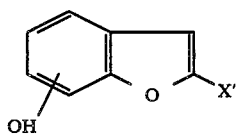

wherein X' is selected from acetyl, carbamoyl, cyano, a lower alkoxycarbonyl, or 1-hydroxyethyl group, by reflux with heating under appropriate catalyst such as, for example, piperidine hydrochloride, piperidine, boron trifluoride.

In case that X is carboxyl group, [2,3-epoxypropoxy]-benzofuran derivative (II) which is obtained from epichlorohydrin and hydroxybenzofuran derivative in which X' is a lower alkoxycarbonyl group in the formula (IX) and having the formula (X):

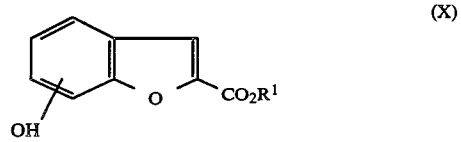

wherein $R^1$ is a lower alkyl group, is hydrolyzed usually at a temperature of $-10°$ to $10°$ C. for about 20–30 minuites to 5 hours using an equimolar to 1.3 times molar amount of an inorganic base such as sodium hydroxide and potassium hydroxide under the presence of water and a suitable lower alcohol such as methanol and ethanol as a solvent.

[The process 2]

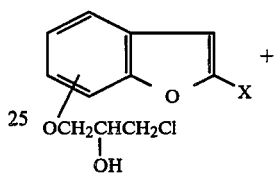

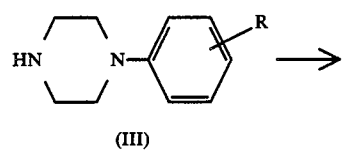

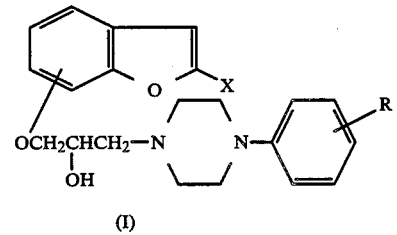

Wherein X and R are the same as above.

This is the process for preparing the compound (I), characterized in that [3-chloro-2-hydroxypropoxy]benzofuran derivative (IV) is condensed with N-phenylpiperazine (III) or the salt thereof.

The above-mentioned reaction is generally carried out by subjecting an equimolar to 1.5 times molar amount of the compound (III) as compared with the compound (IV) to the compound (IV) in an organic solvent. In the above-mentioned reaction, an equimolar to 1.5 times molar amount of base as compared with the compound (IV), such as sodium hydroxide, potassium hydroxide, sodium carbonate, potassium carbonate, trimethylamine and triethylamine, is added to the reaction system when the compound (III) is employed as the acid addition salt. In the reaction procedure, for example, both compound (IV) and compound (III) are heated to react using any organic solvent in the sealed tube, or are refluxed with heating using any organic solvent. Examples of the organic solvent employed are, for example, ethanol, propanol, 2-propanol, butanol, 2-butanol, acetonitrile, tetrahydrofuran, dioxane, dimethoxyethane, dimethylformamide, and the like.

The reaction temperature and the reaction time are not paticularly limited. In general, the reaction is carried out at a temperature of about 50° C. to about 150° C. for about 30 minuites to about 15 hours.

In the above-mentioned reaction, the desired compound (I) is produced in a form of a hydrochloride. This salt may be isolated either as it is or in a form of a free base after being treated with sodium hydroxide, potassium hydroxide and the like.

The separation and the purification of the desired compound (I) may be carried out by means of a conventional procedure such as solvent-extraction, separation by chromatography and crystallization.

In the above-mentioned reaction, [3-chloro-2-hydroxypropoxy]benzofuran derivatives (IV) are novel compounds which have never been described in any literature when X is carbamoyl, cyano, a lower alkoxy carbonyl or carboxyl group. In case that X is acetyl group, see Japanese Examined Patent Publication (KOKOKU) No. 20062/1975. In case that X is 1-hydroxyethyl group, see Japanese Unexamined Patent Publication (KOKAI) No. 89665/1977.

The novel [3-chloro-2-hydroxypropoxy]benzofuran derivatives (IV) except for a case that X is carboxyl group can be produced by shaking a chloroform solution containing [2,3-epoxypropoxy]benzofuran derivative (II) obtained by the process 1 with 12N hydrochloric acid at room temperature for 30 minutes to 1 hour.

In case that X is carboxyl group, [3-chloro-2-hydroxypropoxy]benzofuran derivative in which X is a lower alkoxycarbonyl group and which has the formula (XI):

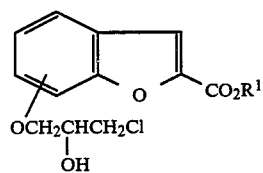

(XI)

wherein R¹ is the same as above, is hydrolized usually at a temperature of 20° to 80° C. for 30 minutes to 3 hours using an equimolar to 10 times molar amount of an inorganic base and using water and a suitable lower alcohol such as methanol and ethanol as a solvent.

[The process 3]

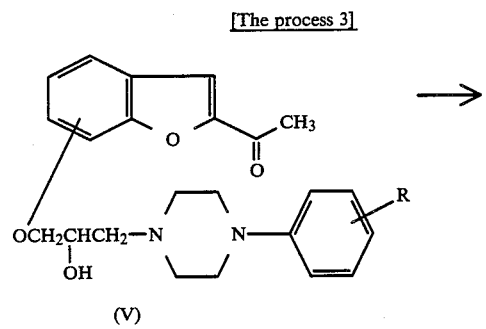

(V)

-continued
[The process 3]

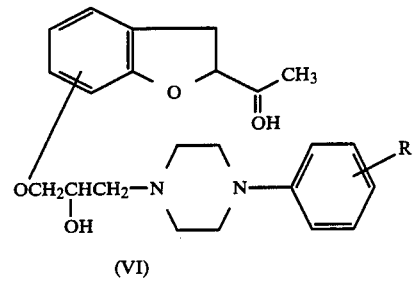

(VI)

wherein R is the same as above.

This is the process for preparing the compound (VI), characterized in that 2-acetylbenzofuran derivative (V) or the salt thereof are reduced by a conventional reducing agent.

The above-mentioned reaction is generally carried out by subjecting an equimolar to 5 times molar amount of any reducing agent as compared with the compound (V) to the compound (V).

Examples of the solvent employed are, for example, methanol, ethanol, dioxane, tetrahydrofuran and the like. Examples of the reducing agent used are, for example, sodium borohydride, lithium aluminum hydride, diborane and the like.

The reaction temperature and the reaction time are not particularly limited. In general, the reaction is carried out at a temperature of about −10° to about 50° C. for about 15 minutes to about 5 hours.

The separation and the purification of the desired compound (VI) may be carried out by means of a conventional procedure such as solvent extraction, separation by chromatography and crystallization.

[The process 4]

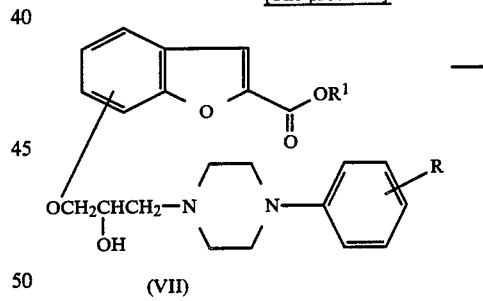

(VII)

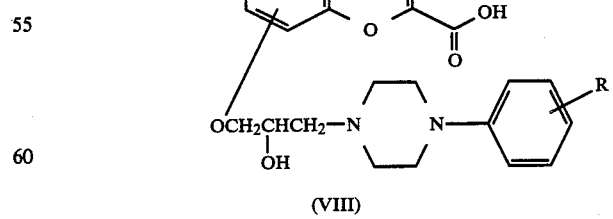

(VIII)

wherein R and R¹ are the same as above.

This is the process for preparing the compound (VIII), characterized in that [2-alkoxycarbonyl]benzofuran derivative (VII) or the salt thereof are hydrolyzed.

The above-mentioned reaction is generally carried out by treating the compound (VII) with acid or alkali in an organic solvent.

Examples of the solvent employed are, for example, water, methanol, ethanol, propanol, 2-propanol, dioxane, tetrahydrofuran and the like. Examples of the acid used are, for example, hydrochloric acid, sulfuric acid, nitric acid and the like. Examples of the alkali employed are, for example, sodium hydroxide, potassium hydroxide, calcium hydroxide, barium hydroxide and the like.

The reaction temperature and the reaction time are not particularly limited and the reaction is generally carried out at a temperature of about 20° to 100° C. for 15 minutes to 5 hours.

The separation and the purification of the desired compound (VIII) may be carried out by means of a conventional procedure such as solvent extraction, separation by chromatography and crystallization.

When a hydrolysis is carried out using the acid, the desired compound may be isolated as a salt of the acid employed. On the other hand, when a hydrolysis is carried out using the alkali, the desired compound may be isolated as a salt of an appropriate inorganic acid or of an organic acid after the desired compound is made into a free base by neutralization.

EFFECT OF THE INVENTION

The compound (I) of the present invention has an excellent α-adrenergic blockade effect (see Test Example 1) and calcium antagonistic effect (see Test Example 2) and shows an excellent antihypertensive activity without tachycardia (see Test Example 3) and an increase of a coronary blood stream (see Test Example 4). Therefore, the compound (I) according to the present invention can be used as the excllent antihypertensive agents with little side-effect.

Moreover, the compound (I) according to the present invention may be used effectively as a curing agent for angina pectoris, a agent for improving a peripheral cardiovascular system and a agent for improving a cardiovascular system in brain.

When the compound (I) of the present invention is used clinically, it is generally injected intravenously or administered orally as a free base or an acid addition salt which is pharmaceutically acceptable as the above-mentioned medicine.

It is suitable that 0.1 to 50 mg/time is injected intravenously several times in a day and 10 to 200 mg/time is administered orally 1 to 3 times in a day to adults, respectively.

The present invention is more particularly described and explained by the following Reference Examples, Examples and Test Examples. It is to be understood that the present invention is not limited to these Reference Examples, Examples and Test examples and various changes and modifications may be made without departing form the spirit and scope of the present invention.

REFERENCE EXAMPLE 1

[Preparation of 2-carbamoyl-7-(2,3-epoxypropoxy)benzofuran]

There was dissolved 17.7 g of 2-carbamoyl-7-hydroxybenzofuran in 200 ml of epichlorohydrin with heating, and thereto 0.5 g of piperidine hydrochloride was added. Thereafter, the mixture was stirred under refluxing for 3 hours. After distilling away epichlorohydrin from the reaction mixture under reduced pressure, 50 ml of methanol was added to the resultant residue to wash the titled product, and the product was taken out by filtration.

Yield: 23 g (quantitative)

Melting point: 198° to 200° C., colorless powder (ethanol)

Elementary analysis for $C_{12}H_{11}NO_4$: Found (%): C 61.76, H 4.81, N 5.88. Calcd. (%): C 61.80, H 4.75, N 6.01.

Infrared absorption spectrum ($\nu_{max}^{KBr}$ cm$^{-1}$): 3450, 3150 and 1700

Mass spectrum (m/e): 233 (M+), 203, 190, 177 and 161

REFERENCE EXAMPLE 2

[Preparation of 2-carbamoyl-6-(2,3-epoxypropoxy)benzofuran]

The procedures of Reference Example 1 were repeated except that 2-carbamoyl-6-hydroxybenzofuran was employed. The resultant residue was purified by silica-gel column-chromatography (silica-gel: 250 g; eluent:ethanol:chloroform=2:100)

Yield: 20 g (86%)

Melting point: 136° to 137° C., colorless needles crystals (ethanol)

Elementary analysis for $C_{12}H_{11}NO_4$: Found (%): C 61.69, H 4.84, N 5.83. Calcd. (%): C 61.80, H 4.75, N 6.01.

Infrared absorption spectrum ($\nu_{max}^{KBr}$ cm$^{-1}$): 3450, 3150 and 1660

Mass spectrum (m/e): 233 (M+), 203, 190, 177 and 161

REFERENCE EXAMPLE 3

[Preparation of 2-carbamoyl-5-(2,3-epoxypropoxy)benzofuran]

The procedures of Reference Example 2 were repeated except that 2-carbamoyl-5-hydroxybenzofuran was employed to give the desired product.

Yield: 19.3 g (83%)

Melting point: 153° to 155° C., colorless needles (ethanol)

Elementary analysis for $C_{12}H_{11}NO_4$: Found (%): C 61.73, H 4.67, N 6.05. Calcd. (%): C 61.80, H 4.75, N 6.01.

Infrared absorption spectrum ($\nu_{max}^{KBr}$ cm$^{-1}$): 3450, 3150 and 1670

Mass spectrum (m/e): 233 (M+), 203, 190, 177 and 161

REFERENCE EXAMPLE 4

[Preparation of 2-cyano-7-(2,3-epoxypropoxy)benzofuran]

There was dissolved 15.9 g of 2-cyano-7-hydroxybenzofuran in 50 ml of epichlorohydrin with heating, and thereto 0.5 g of piperidine hydrochloride was added. Thereafter, the mixture was stirred under refluxing for 2 hours. After distilling away epichlorohydrin from the reaction mixture under reduced pressure, the resultant residue was purified by silica-gel column-chromatography (silica-gel: 250 g; eluent:benzene : ethyl acetate =95:5).

Yield: 12.9 g (65%)

Melting point: 78° C. to 80° C., colorless prisms (benzene : hexane =5 : 1)

Elementary analysis for $C_{12}H_9NO_2$: Found (%): C 72.14, H 4.58, N 6.85. Calcd. (%): C 72.35, H 4.55, N 7.03.

Infrared absorption spectrum ($\nu_{max}^{KBr}$ cm$^{-1}$): 2250
Mass spectrum (m/e): 215 (M$^+$), 185, 172 and 159

REFERENCE EXAMPLE 5

[Preparation of 2-cyano-6-(2,3-epoxypropoxy)benzofuran]

The procedures of Reference Example 4 were repeated except that 2-cyano-6-hydroxybenzofuran was employed to give the desired compound.

Yield: 13.9 g (70%)

Melting point: 90° to 92° C., colorless prisms (benzene : n-hexane =5:1)

Elementary analysis for $C_{12}H_9NO_2$: Found (%): C 72.07, H 4.63, N 7.14. Calcd. (%): C 72.35, H 4.55, N 7.03.

Infrared absorption spectrum ($\nu_{max}^{KBr}$ cm$^{-1}$) 2250
Mass spectrum (m/e): 205 (M$^+$), 185, 172 and 159

REFERENCE EXAMPLE 6

[Preparation of 2-carbamoyl-7-(3-chloro-2-hydroxypropoxy)benzofuran]

There was suspended 2.3 g of 2-carbamoyl-7-(2,3-epoxypropoxy)benzofuran obtained in Reference Example 1 in 70 ml of chloroform, and thereto 15 ml of concentrated hydrochloric acid was added. Thereafter, the mixture was vigorously stirred at room temperature for 15 minutes. After the chloroform layer was washed with water and dried with magnesium sulfate, the solvent was distilled away from the reaction mixture under reduced pressure. The resultant residue was purified by silica-gel chromatography (eluent: 2 % ethanol-chloroform) to give the desired compound.

Yield: 2.2 g (83%)

Melting point: 163° to 164° C., colorless powder (ethyl acetate)

Elementary analysis for $C_{12}H_{12}ClNO_4$: Found (%): C 53.21, H 4.56, N 4.98, Cl 13.25. Calcd. (%): C 53.43, H 4.45, N 5.19, Cl 13.17.

Infrared absorption spectrum ($\nu_{max}^{KBr}$ cm$^{-1}$): 3100 to 3600 and 1660
Mass spectrum (m/e): 269 (M$^+$), 271, 190, 177 and 161

REFERENCE EXAMPLE 7

[Preparation of 2-carbamoyl-6-(3-chloro-2-hydroxypropoxy)benzofuran]

The procedures of Reference Example 6 were repeated except that 2-carbamoyl-6-(2,3-epoxypropoxy)benzofuran obtained in Reference Example 2 was employed to give the desired compound.

Yield: 2.1 g (79%)

Melting point: 109° to 110° C., colorless powder (ethyl acetate)

Elementary analysis for $C_{12}H_{12}ClNO_4$. Found (%): C 33.27, H 4.34, N 5.08, Cl 13.35. Calcd. (%): C 53.43, H 4.45, N 5.19, Cl 13.17.

Infrared absorption spectrum ($\nu_{max}^{KBr}$ cm$^{-1}$): 3100 to 3600 and 1665
Mass spectrum (m/e): 269 (M$^+$), 271, 233, 177 and 161

REFERENCE EXAMPLE 8

[Preparation of 2-carbamoyl-5-(3-chloro-2-hydroxypropoxy)benzofuran]

The procedures of Reference Example 6 were repeated except that 2-carbamoyl-5-(2,3-epoxypropoxy)-benzofuran obtained in Reference Example 3 was employed to give the desired compound.

Yield: 2.0 g (75%)

Melting point: 136° to 138° C., colorless powder (ethyl acetate)

Elementary analysis for $C_{12}H_{12}ClNO_4$: Found (%): C 54.33, H 4.31, N 5.12, Cl 13.36. Calcd. (%): C 54.43, H 4.45, N 5.19, Cl 13.17.

Infrared absorption spectrum ($\nu_{max}^{KBr}$ cm$^{-1}$): 3100 to 3600 and 1680
Mass spectrum (m/e): 269 (M$^+$), 271, 177 and 161

REFERENCE EXAMPLE 9

[Preparation of 7-(2,3-epoxypropoxy)-2-ethoxycarbonylbenzofuran]

There was dissolved 20.6 g of 2-carbamoyl-7-hydroxybenzofuran in 200 ml of epichlorohydrin with heating, and thereto 0.5 g of piperidine hydrochloride was added. Thereafter, the mixture was stirred under refluxing for 5 hours. After distilling away epichlorohydrin from the reaction mixture under reduced pressure, the resultant residue was purified by silica-gel column-chlomatography (eluent: n-hexane: methylene chloride=1:1) to give the colorless oily product.

Yield: 23.6 g (90%)

Elementary analysis for $C_{14}H_{14}O_5$: Found (%): C 64.02, H 5.43. Calcd. (%): C 64.11, H 5.38.

Infrared absorption spectrum ($\nu_{max}^{KBr}$ cm$^{-1}$): 1725
Mass spectrum (m/e): 262 (M$^+$), 231, 220, 207 and 179

REFERENCE EXAMPLE 10

[Preparation of 7-(3-chloro-2-hydroxypropoxy)-2-ethoxycarbonylbenzofuran]

There was dissolved 2.6 g (0.01 mole) of 7-(2,3-epoxypropoxy)-2-ethoxycarbonylbenzofuran obtained in Reference Example 9 in 15 ml of chloroform, and thereto 2 ml of concentrated hydrochloric acid was added. Thereafter, the mixture was vigorously stirred at room temperature for 15 minutes. After the chloroform layer was washed with water, the layer was dried with magnesium sulfate, and then the solvent was distilled away from the reaction mixture under reduced pressure. The resultant residue was purified by silica-gel column-chromatography (eluent:n-hexane:methylene chloride=1:1) to give the desired compound.

Yield: 2.1 g (70%)

Melting point: 95° to 97° C., colorless needles (n-hexane:ether=1:1)

Elementary analysis for $C_{14}H_{15}ClO_5$: Found (%): C 56.03, H 5.11, Cl 11.97. Calcd. (%): C 56.28, H 5.03, Cl 11.89.

Infrared absorption spectrum ($\nu_{max}^{KBr}$ cm$^{-1}$): 3400 and 1720
Mass spectrum (m/e): 300, 298 (M$^+$), 219, 205, 190, 178 and 149

Reference Example 11

[Preparation of
2-carboxy-7-(2,3-epoxypropoxy)benzofuran]

There was dissolved 2.6 g (0.01 mole) of 7-(2,3-epoxypropoxy)-2-ethoxycarbonylbenzofuran obtained in Reference Example 9 in 10 ml of ethanol, and thereto 0.9 g (0.012 mole) of potassium hydroxide in 5 ml of ethanol solution was added dropwise with stirred under cooling with ice. After stirring the mixture for 3 hours the reaction was completed to neutralize the reaction mixture by 2N hydrochloric acid. Thereafter, the solvent was distilled away from the reaction mixture under reduced pressure, the resultant residue was extracted from 30 ml of chloroform. After washing the chloroform layer with water the layer was dried with magnesium sulfate, and then chloroform was distilled away under reduced pressure to give the resultant residue.

The residue was recrystallized from ether-n-hexane (4:1) to give the desired compound.

Yield: 1.8 g (77%)

Melting point: 117° to 119° C., colorless powder

Elementary analysis for $C_{12}H_{10}O_5$: Found (%): C 61.42, H 4.37. Calcd. (%): C 61.54, H 4.30.

Infrared absorption spectrum ($\nu_{max}^{KBr}$ cm$^{-1}$): 3250 to 3600, 2400 to 2750 and 1710

Mass spectrum (m/e): 234 (M+), 202, 190 and 178

Reference Example 12 [Preparation of 2-carboxy-7-(3-chloro-2-hydroxypropoxybenzofuran]

There was dissolved 3 g of 7-(3-chloro-2-hydroxypropoxy)-2-ethoxycarbonylbenzofuran obtained in Reference Example 10 in 10 ml of a 10% sodium hydroxide in ethanol, and the reaction was carried out at 50° C. for 30 minutes. After neutralizing the reaction mixture by 10% hydrochloric acid the solvent was distilled away from the reaction mixture under reduced pressure, and then the resultant residue was extracted from 30 ml of chloroform. After washing the chloroform solution with water, the solution was dried with magnesium sulfate, and then chloroform was distilled away under reduced pressure to give the solid product.

The solid product was recrystallized from benzene-ether (4:1) to give the desired compound.

Yield: 2.5 g (91%)

Melting point: 102° to 103° C.,

Elementary analysis for $C_{12}H_{11}ClO_5$: Found (%): C 53.01, H 4.19, Cl 13.26. Calcd. (%): C 53.23, H 4.07, Cl 13.12.

Infrared absorption spectrum ($\nu_{max}^{KBr}$ cm$^{-1}$): 3250 to 3600, 2400 to 2750 and 1700

Mass spectrum (m/e): 272, 270 (M+), 235 and 159

EXAMPLE 1

[Preparation of 2-acetyl-7-[3-(4-phenylpiperazinyl)-2-hydroxypropoxy]benzofuran and the salt thereof by the process]

There was dissolved 1.2 g (0.005 mole) of 2-acetyl-7-(2,3-epoxypropoxy)benzofuran in 5 ml of dioxane, and thereto 0.9 g (0.0055 mole) of 1-phenylpiperazine was added. Thereafter, the mixture was refluxed with heating for 1.5 hours. After completion of the reaction, the solvent was distilled away under reduced pressure, and then the resultant residue was crystallized from ether and petroleum ether.

Yield: 1.9 g (94%)

Melting point: 79° to 81° C. (colorless powder)

Elementary analysis for $C_{23}H_{26}N_2O_4$: Found (%) : C 69.89, H 6.75, N 7.32. Calcd. (%): C 70.03, H 6.64, N 7.10.

Infrared absorption spectrum ($\nu_{max}^{KBr}$ cm$^{-1}$): 3100 to 3600 and 1680

Nuclear magnetic resonance spectrum δ (CDCl₃): 2.48 to 2.90 (5H, m), 2.53 (3H, S), 2.95 to 3.17 (5H, m), 4.10 (3H, br.s), 6.51 to 7.12 (8H, m) and 7.19 (1H, s)

Mass spectrum (m/e): 394 (M+), 175, 161 and 132

There was dissolved 1.7 g of the obtained free base in 10 ml of ethanol with heating, and thereto an equivolume in heating of 12N hydrochloric acid was added. After distilling away ethanol from the above mixture under reduced pressure, the resulting residue was crystallized from ethanol and a little amount of ether.

Yield: 1.4 g (70%)

Melting point: 178° to 180° C. (colorless powder)

Infrared absorption spectrum ($\nu_{max}^{KBr}$ cm$^{-1}$): 3250, 2300 to 2750 and 1680

Mass spectrum (m/e): 394 (M+), 175, 161, 132 and 120

EXAMPLE 2a

[Preparation of 2-acetyl-7-{2-hydroxy-3-[4-(2-methoxyphenyl)-piperazinyl]-propoxy}benzofuran and the salt thereof by the process 1]

The procedures of Example 1 were repeated except that 1.2 g (0.005 mole) of 2-acetyl-7-(2,3-epoxypropoxy)benzofuran and 1.1 g (0.0055 mole) of 1-(2-methoxyphenyl)piperazine were employed as starting materials. The obtained concentrated residue was crystallized from ethyl acetate.

Yield: 1.9 g (91%)

Melting point: 117° to 119° C. (colorless powder)

Elementary analysis for $C_{24}H_{28}N_2O_5$: Found (%): C 67.65, H 6.82, N 6.54. Calcd. (%): C 67.90, H 6.65, N 6.60.

Infrared absorption spectrum ($\nu_{max}^{KBr}$ cm$^{-1}$): D50 and 1680

Nuclear magnetic resonance spectrum δ (CDCl₃): 2.50 to 2.84 (6H, m), 2.53 (3H, s), 2.85 to 3.10 (4H, m), 3.10 to 3.54 (1H, br.s), 3.74 (3H, s), 4.12 (3H, br.s), 6.54 to 7.10 (7H, m) and 7.18 (1H, s)

Mass spectrum (m/e): 424 (M+), 231, 205, 190, 176 and 161

There was dissolved 1.9 g of the obtained free base in 20 ml of ethanol with heating, and thereto an equivolume in heating of 12N hydrochloric acid was added and was cooled to give the hydrochloride.

Yield: 1.8 g (82%)

Melting point: 215° to 218° C. (colorless powder)

Infrared absorption spectrum ($\nu_{max}^{KBr}$ cm$^{-1}$): 3150 to 3600, 2100 to 2800 and 1670

Mass spectrum (m/e): 424 (M+), 205, 190, 176, 161 and 149

EXAMPLE 2b

[Preparation of 2-acetyl-7-{2-hydroxy-3-[4-(2-methoxyphenyl)-piperazinyl]propoxy}benzofuran by the process 2]

There was dissolved 1.3 g (0.005 mole) of 2-acetyl-7-(3-chloro-2-hydroxypropoxy)benzofuran and 1.1 g (0.0055 mole) of 1-(2-methoxyphenyl)piperazine in 10 ml of dioxane, and then the mixture was refluxed with heating for 6 hours. After completion of the reaction, 2N-NaOH solution was added to give the free base, which was extracted from chloroform. The extract was dried with magnesium sulfate, and then the solvent was distilled away under reduced pressure. The resultant residue was crystallized from ethyl acetate.

Yield: 1.5 g (73%)

The physicochemical properties of the obtained compound were agreed with those obtained in Example 2a.

EXAMPLE 3

[Preparation of 2-acetyl-7-{2-hydroxy-3-[4-(4-methoxyphenyl)-piperazinyl]-propoxy}benzofuran and the salt thereof by the process 1]

There was added 1.2 g (0.005 mole) of 2-acetyl-7-(2,3-epoxypropoxy)benzofuran into 3 ml of ethanol, and thereto a suspended mixture of 1.3 g (0.0055 mole) of 1-(4-methoxy-phenyl)piperazine hydrochloride, 0.56 g (0.0055 mole) of triethylamine and 2 ml of ethanol was added. Thereafter, the mixture was refluxed with heating for 1.5 hours. After completion of the reaction, the solvent was distilled away from the reaction mixture under reduced pressure, and ethyl acetate was added to the resultant residue to crystallize.

Yield: 1.2 g (57%)

Melting point: 117° to 119° C. (light yellow powder)

Elementary analysis for $C_{24}H_{28}N_2O_5$: Found (%): C 67.71, H 6.73, N 6.66. Calcd. (%): C 67.90, H 6.65, N 6.60.

Infrared absorption spectrum ($\nu_{max}^{KBr}$ cm$^{-1}$): 3100 to 3600 and 1675

Nuclear magnetic resonance spectrum $\delta$ (CDCl$_3$): 2.47 to 2.85 (6H, m), 2.52 (3H, s), 2.87 to 3.07 (4H, m), 3.62 (3H, s), 4.10 (3H, br.s), 6.50 to 7.06 (7H, m) and 7.19 (1H, s)

Mass spectrum (m/e): 424 (M+), 205, 176 and 161

There was dissolved 0.9 g of the obtained free base in 10 ml of ethanol with heating, and thereto an equivolume in heating of 12N hydrochloric acid was added. Thereafter, the mixture was cooled to give a hydrochloride.

Yield: 0.9 g (90%)

Melting point: 173° to 175° C. (light yellow powder)

Infrared absorption spectrum ($\nu_{max}^{KBr}$ cm$^{-1}$): 3250, 2150 to 2800 and 1680

Mass spectrum (m/e): 424 (M+), 205, 176 and 161

EXAMPLE 4a

[Preparation of 2-acetyl-6-{2-hydroxy-3-[4-(2-methoxyphenyl)-piperazinyl]-propoxy}benzofuran by the process 1]

The procedures of Example 1 were repeated except that 1.2 g (0.005 mole) of 2-acetyl-6-(2,3-epoxypropoxy)benzofuran and 1.1 g (0.0055 mole) of 1-(2-methoxyphenyl)piperazine were employed as starting materials. The obtained concentrated residue was crystallized from ethyl acetate.

Yield: 1.8 g (86%)

Melting point: 114° to 116° C. (light yellow powder)

Elementary analysis for $C_{24}H_{28}N_2O_5$: Found (%): C 67.78, H 6.74, N 6.85. Calcd. (%): C 67.90, H 6.65, N 6.60.

Infrared absorption spectrum ($\nu_{max}^{KBr}$ cm$^{-1}$): 3500, 3150 and 1675

Nuclear magnetic resonance spectrum $\delta$ (CDCl$_3$): 2.47 to 2.85 (6H, m), 2.49 (3H, s), 2.90 to 3.17 (4H, m), 3.45 (1H, br.s), 3.72 (3H, s), 3.84 to 4.13 (3H, m), 6.59 to 6.75 (4H, m), 6.78 to 6.94 (2H, m), 7.14 (1H, s) and 7.18 (1H, d, J=8 Hz)

Mass spectrum (m/e): 424 (M+), 205, 190, 176 and 161

There was dissolved 1.7 g of the obtained free base in 20 ml of ethanol with heating, and thereto an equivolume in heating of 12N hydrochloric acid was added. Thereafter, the mixture was cooled to give a hydrochloride.

Yield: 1.6 g (78%)

Melting point: 122° to 125° C. (light yellow powder)

Infrared absorption spectrum ($\nu_{max}^{KBr}$ cm$^{-1}$): 3150 to 3600, 2350 to 2800 and 1675

Mass spectrum (m/e): 424 (M+), 205, 190, 176 and 161

EXAMPLE 4b

[Preparation of 2-acetyl-6-{2-hydroxy-3-[4-(2-methoxyphenyl)-piperazinyl]-propoxy}benzofuran by the process 2]

The procedures of Example 2b were repeated except that 1.3 g (0.005 mole) of 2-acetyl-6-(3-choro-2-hydroxypropoxy)benzofuran and 1.1 g (0.0055 mole) of 1-(2-methoxyphenyl)piperazine were employed as starting materials. The obtained concentrated residue was crystallized from ethyl acetate.

Yield: 1.5 g (70%)

The physicochemical properties of the obtained compound were agreed with those obtained in Example 4a.

EXAMPLE 5a

[Preparation of 2-acetyl-5-{2-hydroxy-3-[4-methoxyphenyl)-piperazinyl]-propoxy}benzofuran by the process 1]

The procedures of Example 1 were repeated except that 1.2 g (0.005 mole) of 2-acetyl-5-(2,3-epoxypropoxy)benzofuran and 1.1 g (0.0055 mole) of 1-(2-methoxyphenyl)piperazine were employed as starting materials. The obtained concentrated residue was crystallized from ethyl acetate.

Yield: 2 g (94%)

Melting point: 138° to 140° C. (colorless powder)

Elementary analysis for $C_{24}H_{28}N_2O_5$: Found (%): C 67.74, H 6.69, N 6.51. Calcd. (%): C 67.90, H 6.65, N 6.60.

Infrared absorption spectrum ($\nu_{max}^{KBr}$ cm$^{-1}$): 3450 and 1680

Nuclear magnetic resonance spectrum $\delta$ (CDCl$_3$): 2.42 to 2.81 (6H, m), 2.45 (3H, s), 2.87 to 3.08 (4H, m), 3.70 (3H, s), 3.85 to 4.12 (3H, m), 6.59 to 6.87 (6H, m), 7.15 (1H, s) and 7.26 (1H, d, J=8 Hz)

Mass spectrum (m/e): 424 (M+), 205, 190, 176 and 161

There was dissolved 1.9 g of the obtained free base in 20 ml of ethanol with heating, and thereto an equivolume in heating of 12N hydrochloric acid was added. Thereafter, the mixture was cooled to give a hydrochoride.

Yield: 1.8 g (82%)

Melting point: 184° to 186° C. (colorless powder)

Infrared absorption spectrum ($\nu_{max}^{KBr}$ cm$^{-1}$): 3200 to 3600, 2150 to 2800 and 1665

Mass spectrum (m/e): 424 (M+), 205, 191 and 150

EXAMPLE 5b

[Preparation of 2-acetyl-5-{2-hydroxy-3-[4-methoxyphenyl)-piperazinyl]propoxy}benzofuran by the process 2]

The procedures of Example 2b were repeated except that 1.3 g (0.005 mole) of 2-acetyl-5-(3-choro-2-hydroxypropoxy)benzofuran and 1.1 g (0.0055 mole) of 1-(2-methoxyphenyl)piperazine were employed as starting materials. The obtained concentrated residue was crystallized from ethyl acetate.

Yield: 1.5 g (70%)

The physicochemical properties of the obtained compound were agreed with those obtained in Example 5a.

EXAMPLE 6a

[Preparation of 2-acetyl-7-{2-hydroxy-3-[4-(2-methylphenyl)-piperazinyl]propoxy}benzofuran by the process 1]

The procedures of Example 3 were repeated except that 1.2 g (0.005 mole) of 2-acetyl-7-(2,3-epoxypropoxy)benzofuran and 1.2 g (0.0055 mole) of 1-(2-methylphenyl)piperazine hydrochloride were employed as starting materials. The obtained concentrated residue was crystallized from ethyl acetate and petroleum ether.

Yield: 1.2 g (58%)

Melting point: 89° to 91° C. (light yellow powder)

Elementary analysis for $C_{24}H_{28}N_2O_4$: Found (%): C 70.32, H 6.98, N 6.69. Calcd. (%): C 70.56, H 6.91, N 6.86.

Infrared absorption spectrum ($\nu_{max}^{KBr}$ cm$^{-1}$): 3100 to 3600 and 1680

Nuclear magnetic resonance spectrum $\delta$ (CDCl$_3$): 2.24 (3H, s), 2.49 to 2.80 (6H, m), 2.54 (3H, s), 2.81 to 2.94 (4H, m), 2.96 to 3.42 (1H, br.s), 4.13 (3H, br.s), 6.71 to 7.03 (7H, m) and 7.22 (1H, s)

Mass spectrum (m/e): 408 (M+), 268, 219, 189, 176 and 161

There was dissolved 1.1 g of the obtained free base in 10 ml of ethanol with heating, and thereto an equivolume in heating of 12N hydrochloric acid was added. After distilling away the solvent under reduced pressure, the resultant residue was crystallized from ethanol and ether.

Yield: 1.05 g (81%)

Melting point: 159° to 161° C. (light yellow powder)

Infrared absorption spectrum ($\nu_{max}^{KBr}$ cm$^{-1}$): 3200 to 3600, 2200 to 2800 and 1680

Mass spectrum (m/e): 408 (M+), 189, 176 and 161

EXAMPLE 6b

[Preparation of 2-acetyl-7-{(2-hydroxy-3-[4-(2-methylphenyl)-piperazinyl]propoxy}benzofuran by the process 2]

The procedures of Example 2b were repeated except that 1.3 g (0.005 mole) of 2-acetyl-7-(3-chloro-2-hydroxypropoxy)benzofuran and 1.0 g (0.0055 mole) of 1-(2-methylphenyl)piperazine were employed as starting materials. The obtained concentrated residue was crystallized from ethyl acetate and petroleum ether.

Yield: 1.3 g (65%)

The physicochemical properties of the obtained compound were agreed with those obtained in Example 6a.

EXAMPLE 7

[2-acetyl-5-{2-hydroxy-3-[4-2-methylphenyl)-piperazinyl]-propoxy}benzofuran and the salt thereof by the process 1]

The procedures of Example 3 were repeated except that 1.2 g (0.005 mole) of 2-acetyl-5-(2,3-epoxypropoxy)benzofuran and 1.2 g (0.0055 mole) of 1-(2-methylphenyl)piperazine hydrochloride were employed as starting materials. The obtained concentrated residue was crystallized from ethyl acetate.

Yield: 1.3 g (60%)

Melting point: 125° to 126° C. (light yellow powder)

Elementary analysis for $C_{24}H_{28}N_2O_4$: Found (%): C 70.33, H 6.99, N 6.59. Calcd. (%): C 70.56, H 6.91, N 6.86.

Infrared absorption spectrum ($\nu_{max}^{KBr}$ cm$^{-1}$): 3100 to 3600 and 1680

Nuclear magnetic resonance spectrum $\delta$ (CDCl$_3$): 2.15 (3H, s), 2.24 (3H, s), 2.42 (3H, s), 2.49 to 2.85 (10H, m), 3.73 to 4.00 (3H, m) and 6.45 to 7.06 (8H, m)

Mass spectrum (m/e): 408 (M$^{30}$), 268, 219, 189 and 176

There was dissolved 1.1 g of the obtained free base in 10 ml of ethanol with heating, and thereto an equivolume in heating of 12N hydrochloric acid was added. After distilling away the solvent under reduced pressure, the resultant residue was crystallized from ethanol and ether.

Yield: 1.1 g (83%)

Melting point: 207° to 210° C. (light yellow powder)

Infrared absorption spectrum ($\nu_{max}^{KBr}$ cm$^{-1}$): 3200 to 3600, 2200 to 2800 and 1680

Mass spectrum (m/e): 408 (M+), 189 and 176

EXAMPLE 8

[Preparation of 2-acetyl-7-{3-[4-(3-chlorophenyl)piperazinyl]-2-hydroxypropoxy}benzofuran and the salt thereof by the process 1]

The procedures of Example 3 were repeated except that 1.2 g (0.005 mole) of 2-acetyl-7-(2,3-epoxypropoxy)benzofuran and 1.4 g (0.0055 mole) of 1-(3-chlorophenyl)piperazine were employed as starting materials. The obtained concentrated residue was crystallized from ethyl acetate and petroleum ether.

Yield: 1.1 g (52%)

Melting point: 104° to 106° C. (light yellow powder)

Elementary analysis for $C_{23}H_{25}ClN_2O_4$: Found (%): C 64.08, H 5.81, Cl 8.54, N 6.37. Calcd. (%): C 64.40, H 5.88, Cl 8.27, N 6.53.

Infrared absorption spectrum ($\nu_{max}^{KBr}$ cm$^{-1}$): 3100 to 3600 and 1680

Nuclear magnetic resonance spectrum $\delta$ (CDCl$_3$): 2.42 to 2.85 (6H, m), 2.52 (3H, s), 2.98 to 3.22 (4H, m), 4.11 (3H, br.s), 6.45 to 6.66 (3H, m), 6.70 to 7.04 (4H, m) and 7.20 (1H, s)

Mass spectrum (m/e): 428 (M$^{30}$), 430, 209, 211, 176 and 161

There was dissolved 1 g of the obtained free base in 10 ml of ethanol with heating, and thereto an equivolume in heating of 12N hydrochloric acid was added. After distilling away the solvent under reduced pressure, the obtained residue was crystallized from ethanol and ether.

Yield: 1 g (85%)

Melting point: 203° to 205° C. (light yellow powder)

Infrared absorption spectrum ($\nu_{max}^{KBr}$ cm$^{-1}$): 3300, 2300 to 2800 and 1680

Mass spectrum (m/e): 428 (M$^+$), 430, 209, 211, 176 and 161

EXAMPLE 9

[Preparation of 2-carbamoyl-7-{2-hydroxy-3-[4-(2-methoxyphenyl)-piperazinyl]propoxy}benzofuran by the process 1]

There was suspended 1.2 g (0.005 mole) of 2-carbamoyl-7-(2,3-epoxypropoxy)benzofuran in 15 ml of ethanol, and thereto 1.1 g (0.0055 mole) of 1-(2-methoxyphenyl)piperazine was added. Thereafter, the mixture was refluxed with heating for 2 hours. After completion of the reaction, the solvent was distilled away from the reaction mixture under reduced pressure, and then the resultant residue was crystallized from chloroform and petroleum ether.

Yield: 1.9 g (91%)

Melting point: 166° to 168° C. (colorless powder)

Elementary analysis for $C_{23}H_{27}N_3O_5$: Found (%): C 64.73, H 6.58, N 9.77. Calcd. (%): C 64.92, H 6.40, N 9.88.

Infrared absorption spectrum ($\nu_{max}^{KBr}$ cm$^{-1}$): 3050 to 3600 and 1665

Nuclear magnetic resonance spectrum $\delta$ (CDCl$_3$): 2.46 to 2.84 (6H, m), 2.84 to 3.10 (4H, m), 3.71 (3H, s), 4.09 (3H, br.s), 6.59 to 6.82 (5H, m), 6.88 to 7.00 (2H, m) and 7.20 (1H, s)

Mass spectrum (m/e): 425 (M$^{30}$), 407, 205, 190, 177 and 161

EXAMPLE 9b

[Preparation of 2-carbamoyl-7-{2-hydroxy-3-[4-(2-methoxyphenyl)-piperazinyl]propoxy}benzofuran by the process 2]

There were dissolved 1.3 g (0.005 mole) of 2-carbamoyl-7-(3-chloro-2-hydroxypropoxy)benzofuran and 1.1 g (0.0055 mole) of 1-(2-methoxyphenyl)piperazine in a mixture solvent of 10 ml of dioxane and 10 ml of ethanol, and the resulting mixture was refluxed with heating for 7 hours. After completion of the reaction, 2N-NaOH solution was added to give the free base, which was extracted from chloroform. The extract was dried with magnesium sulfate. Then, the resultant residue obtained by distilling away the solvent under reduced pressure was crystallized from chloroform and petroleum ether.

Yield: 1.6 g (75%)

The physicochemical properties of the obtained compound were agreed with those obtained in Example 8a.

EXAMPLE 10

[Preparation of 2-carbamoyl-7-{2-hydroxy-3-[4-(4-methoxyphenyl)-piperazinyl]porpoxy,}benzofuran by the process 1]

There was dissolved 1.2 g (0.005 mole) of 2-carbamoyl-7-(2,3-epoxypropoxy)benzofuran in 15 ml of ethanol, and thereto a suspended mexture of 1.3 g (0.0055 mole) of 1-(4-methoxyphenyl)piperazine hydrochloride, 0.56 g (0.0055 mole) of triethylamine and 5 ml of ethanol were added, which was refluxed for 2 hours with heating. After completion of the reaction, the solvent was distilled away form the reaction mixture under reduced pressure and the obtained residue was extracted from ethyl acetate. The extract was washed with water and dried with magnesium sulfate. Then, the resultant residue obtained by distilling away the solvent under reduced pressure was crystallized from chloroform and petroleum ether.

Yield: 1.4 g (67%)

Melting point: 181° to 183° C. (colorless powder)

Elementary analysis for $C_{23}H_{27}N_3O_5$: Found (%): C 64.69, H 6.60, N 10.05. Calcd. (%): C 64.92, H 6.40, N 9.88.

Infrared absorption spectrum ($\nu_{max}^{KBr}$ cm$^{-1}$): 3050 to 3600 and 1655

Nuclear magnetic resonance spectrum $\delta$ (CDCl$_3$): 2.45 to 2.83 (6H, m), 2.87 to 3.05 (4H, m), 3.70 (3H, s), 4.05 (3H, br.s), 5.60 to 6.00 (br.s), 6.52 6.71 (5H, m), 6.85 to 6.95 (2H, m) and 7.15 (1H, s)

Mass spectrum (m/e): 425 (M$^+$), 407, 205, 190, 177 and 161

EXAMPLE 11a

[Preparation of 2-carbamoyl-6-{2-hydroxy-3-[4-(2-methoxyphenyl)-piperazinyl]propoxy}benzofuran by process 1]

The procedures of Example 8a were repeated except that 1.2 g (0.005 mole) of 2-carbamoyl-6-(2,3-epoxypropoxy)benzofuran and 1.1 g (0.0055 mole) of 1-(2-methoxyphenyl)piperazine were employed to give the desired compound.

Yield: 2.0 g (93%)

Melting point: 152° to 154° C. (colorless powder)

Elementary analysis for $C_{23}H_{27}N_3O_5$: Found (%): C 64.73, H 6.55, N 9.74. Calcd. (%): C 64.92, H 6.40, N 9.88.

Infrared absorption spectrum ($\nu_{max}^{KBr}$ cm$^{-1}$): 3400, 3200 and 1655

Nuclear magnetic resonance spectrum $\delta$ (CDCl$_3$): 2.55 to 3.10 (10H, m), 3.75 (3H, s), 3.86 to 4.19 (3H, m), 6.70 (br.s), 6.60 to 6.87 (6H, m), 7.20 (H-1, s) and 7.29 (1H, d, J=8 Hz)

Mass spectrum (m/e): 425 (M$^+$), 407, 205, 190, 177, 161 and 150

EXAMPLE 11b

[Preparation of 2-carbamoyl-6-{2-hydroxy-3-[4-(2-methoxyphenyl)-piperazinyl]propoxy}benzofuran by the process 2]

The procedures of Example 9b were repeated except that 1.3 g (0.005 mole) of 2-carbamoyl-6-(3-chloro-2-hydroxypropoxy)benzofuran and 1.1 g (0.0055 mole) of 1-(2-methoxyphenyl)piperazine were employed to give the desired compound.

Yield: 1.5 g (70%)

The physicochemical properties of the obtained compound were agreed with those obtained in Example 11a.

EXAMPLE 12a

[Preparation of 2-carbamoyl-5-{2-hydroxy-3-[4-(2-methoxyphenyl)-piperazinyl-propoxy}benzofuran by the process 1]

The procedures of Example 9a were repeated except that 1.2 g (0.005 mole) of 2-carbamoyl-5-(2,3-epoxypropoxy)benzofuran and 1.1 g (0.0055 mole) of 1-(2-methoxyphenyl)piperazine were employed to give the desired compound.

Yield: 1.9 g (89%)

Melting point: 189° to 191° C. (colorless powder)

Elementary analysis for $C_{23}H_{27}N_3O_5$: Found (%): C 64,76, H 6.58, N 9.94 Calcd. (%): C 64.92, H 6.40, N 9.88.

Infrared absorption spectrum $(\nu_{max}{}^{KBr}$ cm$^{-1})$: 3400, 3200 and 1660

Nuclear magnetic resonance spectrum $\nu$ (CDCl$_3$): 2.50 to 3.12 (10H, m), 3.75 (3H, s), 3.86 to 4.17 (3H, m), 5.75 to 6.50 (br. s), 6.65 to 6.96 (6H, m), 7.21 (1H, s) and 7.17 (1H, d, J=8 Hz)

Mass spectrum (m/e): 425 (M+), 278, 233, 220, 205, 191, 177, 162 and 150

EXAMPLE 12b

[Preparation of 2-carbamoyl-5-{(2-hydroxy-3-[4-(2-methoxyphenyl)-piperazinyl]propoxy}benzofuran by the process 2]

The procedures of Example 8b were repeated except that 1.3 g (0.005 mole) of 2-carbamoyl-5-(3-chloro-2-hydroxypropoxy)benzofuran and 1.1 g (0.0055 mole) of 1-(2-methoxyphenyl)piperazine were employed to give the desired compound.

Yield: 1.5 g (70%)

The physicochemical properties of the obtained compound were agreed with those obtained in Example 12a.

EXAMPLE 13

[Preparation of 2-carbamoyl-7-{2-hydroxy-3-[4-(2-methylphenyl)-piperazinyl]propoxy}benzofuran by the process 1]

The procedures of Example 10 were repeated except that 1.2 g (0.005 mole) of 2-carbamoyl-7-(2,3-epoxypropoxy)benzofuran and 1.2 g (0.0055 mole) of 1-(2-methylphenyl)piperazine hydrochloride were employed. The obtained concentrated residue was crystallized from ethyl acetate and petroleum ether.

Yield: 1.2 g (60%)

Melting point: 94° to 97° C. (colorless powder)

Elementary analysis for $C_{23}H_{27}N_3O_4$: Found (%) : C 67.51, H 6.72, N 10.04. Calcd. (%): C 67.46, H 6.65, N 10.26.

Infrared absorption spectrum $(\nu_{max}{}^{KBr}$ cm$^{-1})$: 3050 to 3600 and 1665

Nuclear magnetic resonance spectrum $\delta$(CDCl$_3$): 2.15 (3H, s), 2.40 to 2.85 (10H, m), 3.92 to 4.23 (3H, m), 5.80 to 6.30 (br.s), 6.55 to 6.98 (7H, m) and 7.14 (1H, s)

Mass spectrum (m/e): 409 (M+), 390, 269, 233, 220, 203, 190, 187 and 161

EXAMPLE 14

[Preparation of 2-carbamoyl-6-{2-hydroxy-3-[4-(2-methylphenyl)-piperazinyl]-propoxy}benzofuran by the process 1]

The procedures of Example 10 were repeated except that 1.2 g (0.005 mole) of 2-carbamoyl-6-(2,3-epoxypropoxy)benzofuran and 1.1 g (0.0055 mole) of 1-(2-methylphenyl)piperazine hydrochloride were employed. The obtained residue was crystallized from ethyl acetate and ether.

Yield: 1.4 g (66%)

Melting point: 86° to 87° C. (colorless powder)

Elementary analysis for $C_{23}H_{27}N_3O_4$: Found (%) : C 67.26, H 6.81, N 10.13. Calcd. (%): C 67.46, H 6.65, N 10.26.

Infrared absorption spectrum $(\nu_{max}{}^{KBr}$ cm$^{-1})$: 3450, 3150 and 1660

Nuclear magnetic resonance spectrum $\delta$(CDCl$_3$): 2.24 (3H, s), 2.45 to 3.00 (9H, m), 3.64 to 3.74 (1H, m), 3.91 to 4.25 (3H, m), 6.25 (br.s), 6.65 to 7.05 (6H, m), 7.21 (1H, s) and 7.29 (1H, d, J=8Hz)

Mass spectrum (m/e): 409 (M+), 269, 233, 189, 177 and 161

EXAMPLE 15

[Preparation of 2-carbamoyl-7-}3-[4-(3-chlorophenyl)piperazinyl]-2-hydroxypropoxy}benzofuran by the process 1]

The procedures of Example 10 were repeated except that 1.2 g (0.005 mole) of 2-carbamoyl-7-(2,3-epoxypropoxy)benzofuran and 1.4 g (0.0055 mole) of 1-(3-chlorophenyl)piperzine hydrochloride were employed. The reaction solution was concentrated to give the crystal. After washing and drying the crystal, it was recrystallized from ethyl acetate.

Yield: 1.1 g (52%)

Melting point: 141° to 144° C. (colorless powder)

Elementary analysis for $C_{22}H_{24}ClN_3O_4$: Found (%) : C 61.22, H 5.64, N 9.57, Cl 8.46. Calcd. (%): C 61.47, H 5.59, N 9.78, Cl 8.27.

Infrared absorption spectrum $(\nu_{max}{}^{KBr}$ cm$^{-1})$: 3050 to 3600 and 1660

Nuclear magnetic resonance spectrum $\delta$(CDCl$_3$): 2.35 to 2.80 (6H, m), 2.82 to 3.07 (4H, m), 3.95 to 4.05 (3H, m), 6.38 to 6.97 (7H, m) and 7.13 (1H, s)

Mass spectrum (m/e): 429 (M+), 269, 233, 220, 209, 190, 177 and 161

EXAMPLE 16

[Preparation of 2-cyano-7-{2-hydroxy-3-[4-(2-methoxyphenyl)-piperazinyl]-propoxy} benzofuran by the process 1]

The procedures of Example 1 were repeated except that 1.1 g (0.005 mole) of 2-cyano-7-(2,3-epoxypropoxy)benzofuran and 1.1 g (0.0055 mole) of 1-(2-methoxyphenyl)piperazine were employed. The obtained residue was crystallized from ethyl acetate and petroleum ether.

Yield: 1.3 g (65%)

Melting point: 109° to 111° C. (colorless powder)

Elementary analysis for $C_{23}H_{25}N_3Ohd 4$: Found (%) : C 67.65, H 6.27, N 10.18. Calcd. (%): C 67.79, H 6.18, N 10.31.

Infrared absorption sepctrum $(\nu_{max}{}^{KBr}$ cm$^{-1})$: 3050 to 3600 and 2250

Nuclear magnetic resonance spectrum $\delta$(CDCl$_3$): 2.50 to 3.10 (10H, m), 3.15 (br.s), 3.72 (3H, s), 4.09 (3H, br.s), 6.58 to 6.91 (5H, m), 6.94 to 7.05 (2H, m) and 7.15 (1H, s)

Mass spectrum (m/e): 407 (M+), 205, 190 and 159

There was dissolved 1 g of the obtained free base in 20 ml of ethanol with heating, and thereto an equivolume in heating of 12N hydrochloric acid was added. After distilling away the solvent under reduced pressure, the resultant residue was crystallized from ethyl acetate.

Yield: 1.1 g (90 %)

Melting point: 194° to 196° C. (colorless needles)

Infrared absorption sepctrum $(\nu_{max}{}^{KBr}$ cm$^{-1})$: 3100, 3200 to 3600 and 2250

Mass spectrum (m/e): 407 (M+), 205, 190 and 159

EXAMPLE 17

[Preparation of 2-cyano-6-{2-hydroxy-3-[4-(2-methoxyphenyl)-piperazinyl]propoxy}benzofuran and the salt thereof by the process 1]

The procedures of Example 1 were repeated except that 1.1 g (0.005 mole) of 2-cyano-6-(2,3-epoxypropoxy)benzofuran and 1.1 g (0.0055 mole) of 1-(2-methoxyphenyl)piperazine were employed. The obtained concentrated residue was crystallized from ether and petroleum ether.

Yield: 1.8 g (88%)
Melting point: 104° to 105° C. (colorless powder)
Elementary analysis for $C_{23}H_{25}N_3O_4$: Found (%) : C 67.71, H 6.27, N 10.14. Calcd. (%): C 67.79, H 6.18, N 10.31.
Infrared absorption sepctrum ($\nu_{max}^{KBr}$ cm$^{-1}$): 3450 and 2250
Nuclear magnetic resonance spectrum $\delta$(CDCl$_3$) 2.47 to 3.06 (10H, m), 3.70 (3H, s), 3.85 to 4.16 (3H, m), 6.57 to 6.81 (6H, m), 7.06 (1H, s) and 7.21 (1H, d, J=8 Hz)
Mass spectrum (m/e): 407 (M$^+$), 205, and 179

There was dissolved 1 g of the obtained free base in 20 ml of ethanol with heating, and thereto an equivolume in heating of 12N hydrochloric acid was added. After distilling away the solvent from the reaction mixture under reduced pressure, the obtained residue was crystallized from ethyl acetate and petroleum ether.

Yield: 1 g (85 %)
Melting point: 220° to 223° C. (colorless powder)
Infrared absorption sepctrum ($\nu_{max}^{KBr}$ cm$^{-1}$): 3150 to 3600, 2100 to 2800 and 2240
Mass spectrum (m/e): 407 (M$^+$), 205, 190 and 159

EXAMPLE 18

[Preparation of 2-ethoxycarbonyl-7-{2-hydroxy-3-[4-(2-methoxyphenyl)-piperazinyl]propoxy}benzofuran and the salt thereof by the process 1]

The procedures of Example 1 were repeated except that 1.3 g (0.005 mole) of 7-(2,3-epoxypropoxy)2-ethoxycarbonylbenzofuran and 1.1 g (0.0055 mole) of 1-(2-methoxyphenyl)piperazine were employed. The obtained concentrated residue was crystallized from ether and petroleum ether.

Yield: 2 g (90%)
Melting point: 90° to 91° C. (colorless powder)
Elementary analysis for $C_{25}H_{30}N_2O_6$: Found (%) : C 65.88, H 6.80, N 6.36: Calcd. (%): C 60.06, H 6.65, N 6.16: Infrared absorption spectrum ($\nu_{max}^{KBr}$ cm$^{-1}$): 3450 and 1720
Nuclear magnetic resonance spectrum $\delta$(CDCl$_3$): 1.31 (3H, t, J=7 Hz), 2.50 to 2.85 (6H, m), 2.90 to 3.12 (4H, m), 3.60 (br.s), 4.15 (3H, br.s) 4.31 (2H, q, J=7 Hz), 6.58 to 6.90 (5H, m), 6.92 to 7.06 (2H, m) and 7.26 (1H, s)
Mass spectrum (m/e): 454 (M$^+$), 205 and 190

There was dissolved 2.4 g of the obtained free base in 20 ml of ethanol with heating, and thereto an equivolume in heating of 12N hydrochloric acid was added. After distilling away the solvent from the reaction mixture under reduced pressure, the obtained residue was crystallized from ethanol and a little amount of ether.

Yield: 2.1 g (80%)
Melting point: 203° to 205° C. (colorless powder)
Infrared absorption sepctrum ($\nu_{max}^{KBr}$ cm$^{-1}$): 3150 to 3600 and 1725
Mass spectrum (m/e): 454 (M$^+$), 409, 205 and 190

EXAMPLE 19

[Preparation of 2-ethoxycarbonyl-5-{2-hydroxy-3-[4-(2-methoxyphenyl)piperrazinyl]propoxy}benzofuran and the salt thereof by the process 1]

The procedures of Example 1 were repeated except that 1.3 g (0.005 mole) of 5-(2,3-epoxypropoxy)-2-ethoxycarbonylbenzofuran and 1.0 g (0.0055 mole) of 1-(2-methoxyphenyl)piperazine were employed. The obtained concentrated residue was purified by silica-gel column-chromatography (eluting solvent: methylene chloride).

Yield: 1.9 g (88%) (colorless oily product)
Elementary analysis for $C_{25}H_{30}N_2O_4$: Found (%) : C 70.81, H 7.23, N 6.35. Calcd. (%): C 71.06, H 7.16, N 6.63.
Infrared absorption spectrum ($\nu/\max^{neat}$ cm$^{-1}$): 3450 and 1720
Nuclear magnetic resonance spectrum $\delta$(CDCl$_3$): 1.34 (3H, t, J=7 Hz), 2.30 to 3.05 (10H, m), 3.61 (3H, s), 3.68 to 4.00 (3H, m), 4.14 (2H, q, J=7 Hz) and 6.30 to 7.05 (8H, m)
Mass spectrum (m/e): 454 (M$^+$), 205 and 190

There was dissolved 2.4 g of the obtained free base in 20 ml of ethanol, and thereto an equivolume in heating of 12N hydrochloric acid was added. After distilling away the solvent under reduced pressure, the resultant residue was crystallized from ethanol and a little amount of ether.

Yield: 2.0 g (78%)
Melting point: 197° to 201° C. (colorless powder)
Infrared absorption spectrum ($\nu_{max}^{KBr}$ cm$^{-1}$): 3150 to 3600 and 1725
Mass spectrum (m/e): 454 (M$^+$), 409, 205 and 190

EXAMPLE 20

[Preparation of 2-ethoxycarbonyl-5-{2-hydroxy-3-[4-(2-methylphenyl)-piperazinyl]propoxy}benzofuran and the salt thereof by the process 1]

The procedures of Example 3 were repeated except that 1.3 g (0.005 mole) of 5-(2,3-epoxypropoxy)-2-ethoxycarbonylbenzofuran and 1.1 g (0.0055 mole) of 1-(2-methylphenyl)piperazine hydrochloride were employed. The reaction mixture was concentrated and was purified by silica-gel column-chromatography (eluting solvent: methylene chloride).

Yield: 1.5 g (65%) (colorless oily product)
Elementary analysis for $C_{25}H_{30}N_2O_6$: Found (%) : C 73.62, H 7.63, N 6.77. Calcd. (%): C 73.86, H 7.44, N 6.89.
Infrared absorption spectrum ($\nu$neat/max cm$^{-1}$): 3450 and 1720
Nuclear magnetic resonance spectrum $\delta$(CDCl$_3$): 1.34 (3H, t, J=7 Hz), 2.16 (3H, s), 2.40 to 2.85 (10H, m), 3.73 to 3.90 (3H, m), 4.13 (2H, q, J=7 Hz) and 6.45 to 7.10 (8H, m)
Mass spectrum (m/e): 438 (M$^+$), 205 and 190

There was dissolved 2.2 g of the obtained free base in 20 ml of ethanol, and thereto an equivolume in heating of 12N hydrochloric acid was added. After distilling away the solvent from the reaction mixture under reduced pressure, the obtained residue was crystallized from ethanol and a little amount of ether.

Yield: 1.7 g (71%)

Melting point: 172° to 175° C. (colorless powder)

Infrared absorption spectrum ($\nu_{max}^{KBr}$ cm$^{-1}$): 3150 to 3600 and 1725

Mass spectrum (m/e): 438 (m+), 393, 205 and 190

EXAMPLE 21A

[Preparation of 2-carboxy-7-2-hydroxy-3-[4-(2-methoxyphenyl)-piperazinyl]propoxy}-benzofuran and the salt thereof by the process 4]

There was dissolved 2.3 g (0.0054 mole) of 2-ethyoxycarbonyl-7-2-hydroxy-3-[4-(2-methoxyphenyl)-piperazinyl]propoxy benzofuran obtained in Example 18 in 50 ml of ethanol, thereto 0.5 g of sodium hydroxide was added, and the resulting mixture was refluxed with heating for 2 hours. After completion of the reaction, an equal amount at cooling with ice of 12N hydrochloric acid was added for neutralizing. The solvent was distilled away under reduced pressure to give the crude free base, and thereto 30 ml of ethanol was added to dissolve the free base with heating. After removing the insoluble residue, excessive 12N hydrochloric acid was added to the solution to give the hydrochloride. After 15 minutes, the solvent was distilled away under reduced pressure. The obtained residue was crystallized from 2-propanol to give the desired compound.

Yield: 1.8 g (85 %)

Melting point: 169° to 174° C. (colorless powder)

Infrared absorption spectrum ($\nu_{max}^{KBr}$ cm$^{-1}$): 3200 to 3600, 2100 to 2750 and 1715

Nuclear magnetic resonance spectrum $\delta$(CDCl$_3$): 3.56 to 3.68 (3H, m), 3.87 (3H, s), 3.92 (6H, br.s), 4.15 to 4.27 (2H, br, d), 4.45 to 4.65 (2H, m), 6.78 to 7.20 (6H, m), 7.35 (1H, s) and 7.30 to 7.45 (1H, m)

Mass spectrum (m/e): 426 (M+), 381, 284, 205, 190, 178, 162 and 150

EXAMPLE 21b

[Preparation of 2-carboxy-7-{2-hydroxy-3-[4-(2-methoxyphenyl)-piperazinyl]propoxy}benzofuran and the salt thereof by the process 1]

The procedures of Example 1 were repeated except that 2.3 g (0.005 mole) of 2-carboxy-7-(2,3-epoxypropoxy)benzofuran and 1.1 g (0.0055 mole) of 1-(2-methoxyphenyl)piperazine were employed. The residue obtained by the concentration of the reaction solution under reduced pressure was crystallized from ethyl acetate.

Yield: 1.9 g (88%)

Melting point: 78° to 80° C. (light yellow powder)

Elementary analysis for $C_{23}H_{26}N_2O_6$: Found (%) : C 64.52, H 6.24, N 6.71. Calcd. (%): C 64.77, H 6.15, N 6.57.

Infrared absorption spectrum ($\nu_{max}^{KBr}$ cm$^{-1}$): 3200 to 3600, 2250 to 2750 and 1715

Mass spectrum (m/e): 426 (M+), 381, 284, 205, 190 and 178

There was dissolved 2.1 g of the obtained free base in 20 ml of ethanol, and thereto an equal amount in heating of 12N hydrochloric acid was added. Then, ethanol was distilled away under reduced pressure and the obtained residue was crystallized from 2-propanol.

Yield: 2 g (80%)

The physicochemical properties of the obtained compound were agreed with those obtained in Example 21a.

EXAMPLE 22a

[Preparation of 2-(1-hydroxyethyl)-7-{2-hydroxy-3-[4-(2-methoxyphenyl)piperazinyl]propoxy}benzofuran by the process 3]

There was dissolved 4.3 g (0.01 mole) of 2-acetyl-7-{2-hydroxy-3-[4-(2-methoxyphenyl)piperazinyl]-propoxy}benzofuran in 50 ml of ethanol, and thereto 0.35 g of sodium borohydride was gradually added with cooling with ice. After stirring 1 hour, aceton was added to decompose the excess sodium borohydride and the solvent was distilled away under reduced pressure. The residue was extracted from ethyl acetate and the obtained extract was dried with magnesium after washing with water. Ethyl acetate was distilled away under reduced pressure and the obtained residue was crystallized from ethyl acetate.

Yield: 2.8 g (65%)

Melting point: 102° to 105° C. (colorless powder)

Elementary analysis for $C_{24}HN_2O_5$: Found (%) : C 67.43, H 7.15, N 6.48. Calcd. (%): C 67.58, H 7.09, N 6.57.

Infrared absorption spectrum ($\nu_{max}^{KBr}$ cm$^{-1}$) 3100 to 3600 and 2400 to 2800

Nuclear magnetic resonance spectrum $\delta$(CDCl$_3$): 1.55 (3H, d, J=6 Hz), 3.13 to 3.50 (8H, m), 3.69 (3H, s), 3.85 to 4.23 (3H, m), 4.50 to 4.75 (2H, m), 4.84 (1H, q, J=6 Hz), 6.30 (1H, s) and 6.38 to 6.95 (7H, m)

Mass spectrum (m/e): 426 (M+), 408, 205 and 190

EXAMPLE 22b

[Preparation of 2-(1-hydroxyethyl)-7-{2-hydroxy-3-[4-(2-methoxyphenyl)piperazinyl]propoxy}benzofuran by the process 1]

The procedures of Example 1 were repeated except that 1.2 g (0.005 mole) of 7-(2,3-epoxypropoxy)-(1-hydroxyethyl)benzofuran and 1.1 g (0.0055 mole) of 1-(2-methoxyphenyl)piperazine were employed. The obtained concentrated residue was crystallized from ether acetate.

Yield: 1.9 g (90%)

The physicochemical properties of the obtained compound were agreed with those obtained in Example 22a.

EXAMPLE 23a

[Preparation of 2-(1-hydroxyethyl)-7-{2-hydroxy-3-[4-(2-methylphenyl)piperazinyl]propoxy}benzofuran by the process 3]

The procedures of Example 22a were repeated except that 4.1 g (0.01 mole) of 2-acetyl-7-{2-hydroxy-3-[4-(2-methylphenyl)piperazinyl]propoxy}benzofuran obtained in Example 6a or 6b was employed. The obtained residue was crystallized from ethel acetate and ether.

Yield: 2.8 g (68%)

Melting point: 129° to 130° C. (colorless powder)

Elementary analysis for $C_{24}HN_2O_4$: Found (%) : C 69.98, H 7.52, N 6.56. Calcd. (%): C 70.22, H 7.37, N 6.82.

Infrared absorption spectrum ($\nu_{max}^{KBr}$ cm$^{-1}$): 3100 to 3600 and 2500 to 2800

Nuclear magnetic resonance spectrum δ(CDCl₃) 1.54 (3H, d, J=6Hz), 2.13 (3H, s), 2.18 to 3.22 (8H, m), 3.85 to 4.25 (3H, m), 4.51 to 4.79 (2H, m), 4.84 (1H, q, J=6Hz), 6.31 (1H, s), 6.39 to 6.56 (1H, m) and 6.60 to 6.98 (6H, m)

Mass spectrum (m/e): 410 (M+), 392, 189, 174 and 146

EXAMPLE 23b

[Preparation of 2-(1-hydroxyethyl)-7-{2-hydroxy-3-[4-(2-methylphenyl)piperazinyl]propoxy}benzofuran by the process 2]

The procedures of Example 2b were repeated except that 1.3 g (0.005 mole) of 2-(1-hydroxyethyl)-7-(3-chloro-2-hydroxypropoxy)benzofuran and 1.0 g (0.0055 mole) of 1-(2-methoxyphenyl)piperazine were employed. The obtained residue was crystallized from ethyl acetate and ether.

Yield: 1.8 g (88%)

The physicochemical properties of the obtained compound were agreed with those obtained in Example 2a.

EXAMPLE 24

A tablet of 100 mg having the following composition was prepared.

| (component) | (mg) |
| --- | --- |
| 2-acetyl-7-{2-hydroxy-3-[4-(2-methoxyphenyl)-piperazinyl]propoxy}benzofuran hydrochloride | 10 |
| lactose | 25 |
| cornstarch | 45 |
| microcrystalline cellulose | 15 |
| methyl cellulose | 3 |
| calcium stearate | 2 |

EXAMPLE 25

A capsule of 100 mg having the following composition was prepared by filling the mixture of the components in capsule 5.

| (component) | (mg) |
| --- | --- |
| 2-carbamoyl-7-{2-hydroxy-3-[4-(2-methoxyphenyl)-piperazinyl]propoxy}benzofuran | 10 |
| lactose | 45 |
| cornstarch | 35 |
| microcrystalline cellulose | 8 |
| calcium stearate | 2 |

EXAMPLE 26

The following components were mixed together. After making the core by a slug machine, it was granulated and screened. Thereafter, masking was made with Tc-5R (film coatings) and granules of 500 mg having 20 to 40 meshes were prepared.

| (component) | (mg) |
| --- | --- |
| 2-acetyl-5-{2-hydroxy-3-[4-(2-methoxylphenyl)-piperazinyl]propoxy}benzofuran hydrochloride | 10 |
| lactose | 355 |
| calcium hydrogenphosphate | 80 |
| microcrystalline cellulose | 40 |
| calcium stearate | 5 |
| Tc-5R | 10 |

EXAMPLE 27

According to the following formulation the procedures in Example 23 were repeated to prepare a subtilized granule of 500 mg having 50 to 100 meshes.

| (component) | (mg) |
| --- | --- |
| 2-acetyl-7-{2-hydroxy-3-[4-(2-methylphenyl)-piperazinyl]propoxy}benzofuran hydrochloride | 10 |
| lactose | 365 |
| calcium hydrogenphosphate | 80 |
| microcrystalline cellulose | 30 |
| calcium stearate | 5 |
| Tc-5R | 10 |

EXAMPLE 28

There was dissolved 1 mg of 2-acetyl-7-{2-hydroxy-3-[4-(2-methoxyphenyl)piperazinyl]propoxy}benzofuran hydrochloride in 1 ml of a physiologic salt solution and the solution was adjusted at pH 7.0 to give an injection.

TEST EXAMPLE 1

[α-Adrenergic blockade effect]

Using a vas deferens specimen taken from six weeks old Wister male rat, a contraction response by noradrenalin was measured as a dose-response curve according to Magnus method and the antagonistic activity for each test compound was indicated as pA₂ value, which means a negative logarithm of a dose of an antagonistic agent required for parallelly shifting a dose-response curve of an agonist two times toward a higher concentration side. For the purpose of a comparison, the same experiment as mentioned above was carried out on both Phentolamine which was commonly used as an α-adrenergic blocking agent and Labetalol which was commonly used as an α, β-adrenergic blocking agent. The results were shown in Table 1.

[Calcium antagonistic effect]

Using a spiral blood vessel specimen taken from a thoracic aorta of Hartly male giunea pig weighed 400 to 600 g, a contraction response by calcium was measured as a dose-response curve according to Magnus method and the antagonistic activity for each test compound was indicated as above-mentioned pA₂ value. For the purpose of a comparison, the same experiment as mentioned above was carried out on Diltiazem which was commonly used as a calcium antagonistic agent. The results were shown in Table 1.

TABLE 1

| Test compound | α-Adrenergic blockade effect, pA₂ value (relative ratio as compared with Phentolamine) | Calcium antagomstic effect, pA₂ value (relative ratio as compared with Diltiazem) |
| --- | --- | --- |
| Ex. 1 (HCl salt) | 6.68 ± 0.04 (1/1.3) | 5.53 ± 0.07 (1/32.4) |
| Ex. 2 (HCl salt) | 7.41 ± 0.07 (4.1) | 6.71 ± 0.11 (1/2.1) |

TABLE 1-continued

| Test compound | α-Adrenergic blockade effect, pA₂ value (relative ratio as compared with Phentolamine) | Calcium antagomstic effect, pA₂ value (relative ratio as compared with Diltiazem) |
|---|---|---|
| Ex. 3 (HCl salt) | 6.34 ± 0.04 (1/2.9) | 6.20 ± 0.12 (1/6.9) |
| Ex. 4 (HCl salt) | 7.65 ± 0.03 (7.1) | 6.28 ± 0.17 (1/5.8) |
| Ex. 5 (HCl salt) | 7.31 ± 0.05 (3.2) | 7.33 ± 0.20 (1.9) |
| Ex. 6 (HCl salt) | 7.35 ± 0.09 (3.6) | 6.33 ± 0.12 (1/5.1) |
| Ex. 7 (HCl salt) | 6.66 ± 0.06 (1/1.4) | 6.20 ± 0.15 (1/6.9) |
| Ex. 8 (HCl salt) | 6.33 ± 0.05 (1/3.0) | 7.07 ± 0.13 (1.1) |
| Ex. 9 | 7.56 ± 0.04 (5.8) | 6.20 ± 0.07 (1/6.9) |
| Ex. 10 | 7.06 ± 0.06 (1.8) | 5.90 ± 0.17 (1/13.8) |
| Ex. 11 | 7.24 ± 0.05 (2.8) | 6.80 ± 0.10 (1/1.7) |
| Ex. 12 | 7.00 ± 0.03 (1.6) | 5.93 ± 0.11 (1/12.9) |
| Ex. 13 | 6.62 ± 0.03 (1/1.5) | 5.87 ± 0.08 (1/14.8) |
| Ex. 14 | 6.96 ± 0.06 (1.4) | 6.74 ± 0.06 (1/2) |
| Ex. 15 | 5.52 ± 0.03 (1/19.1) | 6.40 ± 0.23 (1/4.4) |
| Ex. 16 (HCl salt) | 7.37 ± 0.03 (3.7) | 6.29 ± 0.12 (1/5.6) |
| Ex. 17 (HCl salt) | 6.69 ± 0.04 (1/1.3) | 6.94 ± 0.11 (1/1.3) |
| Ex. 18 (HCl salt) | 7.13 ± 0.05 (2.1) | 6.68 ± 0.13 (1/2.3) |
| Ex. 19 (HCl salt) | 6.72 ± 0.03 (1/1.2) | 5.28 ± 0.14 (1/54.5) |
| Ex. 20 (HCl salt) | 6.46 ± 0.09 (1/2.2) | 4.88 ± 0.70 (1/14.5) |
| Ex. 21 (HCl salt) | 6.45 ± 0.03 (1/2.2) | 5.48 ± 0.06 (1/36.3) |
| Ex. 22 | 7.30 ± 0.03 (3.2) | 5.98 ± 0.20 (1/11.5) |
| Ex. 23 | 7.11 ± 0.05 (2.0) | 6.23 ± 0.10 (1/6.5) |
| Phentolamine | 6.80 ± 0.07 (1.0) | — |
| Labetalol | 5.82 ± 0.10 (1/9.5) | — |
| Diltiazem | — | 7.04 ± 0.07 (1.0) |

TEXT EXAMPLE 3

[Antihypertensive effect and effect on a heart rate on rat suffering from a spontaneously hypertensive rat (SHR)]

The experiment was carried out using SHR which had a systolic pressure of not less than 170 mmHg. A blood pressure was measured under no anesthetic condition by means of an apparatus for recording a blood pressure of a tail artery and a heart rate (Riken Kaihatsu Co., Ltd.) (PS-802) and at the same time a heart rate was also measured.

Each of test compounds was dissolved or suspended in an aqueous solution containing 5% by weight of acasia and the obtained solution or suspension was administered once orally to SHR which had been kept under a fast condition for one night. A blood pressure and a heart rate were measured before administration and after one hour, three hours, five hours and seven hours of it and the maximum value of changes were calculated by comparing the value measured before administration with the value measured after administration.

For the purpose of a comparison, the same experiment as mentioned above was carried out on both Labetalol and Diltiazem as mentioned above.

With respect to a dosage, 100 mg/kg and 10 mg/kg as to compounds obtained by Examples 2, 5, 6, 9 and 18 to 23 were respectively administered, 100 mg/kg as to compounds obtained by Examples 1, 3, 4, 7 and 10 to 17 was respectively administered. The results were shown in Table 2 and 3.

TABLE 2

| Test compound | Maximum value of change (100 mg/kg, po) | | Maximum value of change (10 mg/kg, po) | |
|---|---|---|---|---|
| | Systolic pressure (mmHg) | Heart rate (beats/min) | Systolic pressure (mmHg) | Heart rate (beats/min) |
| Ex. 2 | −72.4 ± 8.9 | −155.6 ± 15.5 | −54.8 ± 11.2 | −121.7 ± 15 |
| Ex. 5 | −101.3 ± 5.2 | −143.4 ± 34.2 | −56.3 ± 6.0 | −49.2 ± 28.0 |
| Ex. 6 | −90.3 ± 9.2 | −135.8 ± 17.0 | −71.7 ± 4.9 | −70.0 ± 20.3 |
| Ex. 7 | −117.5 ± 12.6 | −51.3 ± 20.2 | −86.4 ± 8.6 | −45.0 ± 17.2 |
| Ex. 9 | −75.6 ± 2.4 | −69.2 ± 12.1 | −61.2 ± 4.3 | −154.2 ± 17.3 |
| Ex. 18 | −65.1 ± 5.5 | −138.3 ± 25.4 | −35.8 ± 4.6 | −96.7 ± 35.1 |
| Ex. 19 | −60.1 ± 10.8 | −73.4 ± 19.6 | −37.6 ± 9.0 | −68.4 ± 45.1 |
| Ex. 20 | −80.7 ± 13.6 | −87.5 ± 17.7 | −57.5 ± 12.5 | −81.1 ± 22.2 |
| Ex. 21 | −73.8 ± 9.9 | −25.7 ± 16.4 | −46.9 ± 6.3 | −5.8 ± 8.7 |
| Ex. 22 | −69.5 ± 7.9 | −160.2 ± 19.8 | −42.8 ± 6.7 | −149.2 ± 15.3 |
| Ex. 23 | −73.1 ± 9.2 | −131.4 ± 22.3 | −54.9 ± 9.4 | −93.4 ± 17.6 |
| Labetalol | −55.0 ± 9.1 | −125.2 ± 25.6 | −32.9 ± 12.9 | −122.5 ± 37.5 |
| Diltiazem | −79.9 ± 11.6 | −136.7 ± 34.2 | −12.8 ± 5.7 | −140.0 ± 27.5 |

TABLE 3

| Test compound | Maximum value of change (100 mg/kg, po) | |
|---|---|---|
| | Systolic pressure (mmHg) | Heart rate (beats/min) |
| Ex.1 (HCl salt) | −74.6 ± 5.6 | −105.8 ± 3.4 |
| Ex. 3 (HCl salt) | −22.9 ± 1.7 | −200.0 ± 28.4 |
| Ex. 4 (HCl salt) | −114.2 ± 1.7 | −172.5 ± 23.9 |
| Ex. 8 (HCl salt) | −44.2 ± 8.4 | −98.4 ± 17.2 |
| Ex. 10 | −97.9 ± 4.0 | −80.0 ± 37.6 |
| Ex. 11 | −78.8 ± 7.6 | −126.5 ± 27.3 |
| Ex. 12 | −100.2 ± 3.9 | −110.0 ± 20.0 |
| Ex. 13 | −97.0 ± 9.8 | −80.0 ± 16.6 |
| Ex. 14 | −67.3 ± 6.8 | −132.9 ± 28.8 |
| Ex. 15 | −79.9 ± 11.9 | −100.0 ± 19.5 |
| Ex. 16 (HCl salt) | −13.3 ± 4.6 | −189.6 ± 26.8 |
| Ex. 17 (HCl salt) | −40.5 ± 6.6 | −154.5 ± 21.1 |
| Labetalol | −55.0 ± 9.1 | −125.2 ± 25.6 |

TABLE 3-continued

| Test compound | Maximum value of change (100 mg/kg, po) | |
|---|---|---|
| | Systolic pressure (mmHg) | Heart rate (beats/min) |
| Diltiazem | −79.9 ± 11.6 | −136.7 ± 34.2 |

TEST EXAMPLE 4

[Increasing effect on a coronary blood flow]

Adult dog weighed 9 to 13 kg which was anesthetized intravenously with 30 mg/kg of pentobarbiturate was used for this experiment. The animal was cut open at a chest under a condition of an artificial respiration. After an intravenous injection of 1000 U/kg of heparin, a glass cannula was inserted into coronary ramus circumflexus by way of a left subclavina artery and a perfusion was carried out with blood introduced from a right carotid artery. A blood flow was measured by means of a electromagnetic flowmeter set up at a perfusion channel.

Each of test compounds was dissolved in a physiologic salt solution and the solution was administered once into a perfusion channel. An increase of a coronary blood flow was indicated as a percentage of an increasing rate.

For the purpose of a comparison, the same experiment as mentioned above was carried out on Papavelin which was commonly used as coronary vasodilator.

The results were shown in Table 4.

TABLE 4

| Test compound | Increasing rated of coronary blood flow when administered with a 1 mg (%) |
|---|---|
| Ex. 2 (HCl salt) | 88.4 ± 14.2 |
| Ex. 5 (HCl salt) | 107.5 ± 6.5 |
| Ex. 8 (HCl salt) | 96.3 ± 13.1 |
| Ex. 9 | 105.6 ± 11.8 |
| Ex. 22 | 87.7 ± 9.4 |
| papavelin | 136.3 ± 27.0 |

TEST EXAMPLE 5

[Accute toxicity test (LD$_{50}$ value)]

The experiment was carried out using six weeks old ddy male mice.

Each of test compounds was suspended in an aqueous solution containing 5% by weight of acasia and the suspension was administered compulsorily once orally with a gastric probe. Within six hours after the start of the administration, the behavior of tested mice were observed consecutively. Thereafter, the observation was made at an interval of twenty four hours during 7 days and an accumulative number of deaths seventh day since the start of the administration was measured.

LD$_{50}$ value was calculated according to the Litchfield-Wilcoxon method. The results were shown in Table 5.

TABLE 5

| Test compound | LD$_{50}$ (mg/kg) |
|---|---|
| Ex. 1 (HCl salt) | >1000 |
| Ex. 2 | >1500 |
| Ex. 3 (HCl salt) | 700 |
| Ex. 4 (HCl salt) | >1000 |
| Ex. 5 (HCl salt) | >1500 |
| Ex. 6 (HCl salt) | >1500 |
| Ex. 7 (HCl salt) | >2000 |

TABLE 5-continued

| Test compound | LD$_{50}$ (mg/kg) |
|---|---|
| Ex. 8 (HCl salt) | >1000 |
| Ex. 9 | >1500 |
| Ex. 10 | 1100 |
| Ex. 11 | >1500 |
| Ex. 12 | >1500 |
| Ex. 13 | >1500 |
| Ex. 14 | >1000 |
| Ex. 15 | >1000 |
| Ex. 16 (HCl salt) | 900 |
| Ex. 17 (HCl salt) | 900 |
| Ex. 18 (HCl salt) | >1000 |
| Ex. 19 (HCl salt) | >1500 |
| Ex. 20 (HCl salt) | >1500 |
| Ex. 21 (HCl salt) | >1000 |
| Ex. 22 | >1500 |
| Ex. 23 | >1000 |

What we claim is:

1. A [2-hydroxy-3-(4-phenylpiperazinyl)propoxyl]-benzofuran compound having the formula (I)

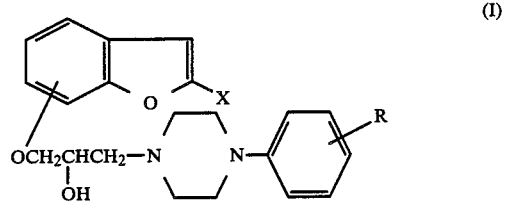

wherein X is acetyl, carbamoyl, cyano, a lower alkoxycarbonyl, carboxyl or 1-hydroxyethyl group, R is hydrogen atom, a lower alkoxy group, a lower alkyl group or a halogen atom; R is attached to an arbitrary position of ortho-position, meta-position and para-position to N-phenyl group, and the group having the formula:

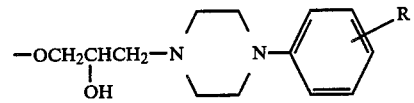

in the formula (I) is attached to an arbitrary position of 4, 5, 6 and 7 positions to the benzofuran ring, or the pharmaceutically acceptable acid addition salts thereof.

2. The compound or the pharmaceutically acceptable acid addition salts thereof of claim 1, wherein, in said formula (I), X is an acetyl group.

3. The compound of claim 2, wherein said derivative is 2-acetyl-7-[3-(4-phenylpiperazinyl)-2-hydroxy]-propoxy benzofuran, or the pharmaceutically acceptable acid addition salts thereof.

4. The compound of claim 2, wherein said derivative is 2-acetyl-7-{2-hydroxy-3-[4-(2-methoxyphenyl)-piperazinyl]propoxy}benzofuran, or the pharmaceutically acceptable acid addition salts thereof.

5. The compound of claim 2, wherein said compound is 2-acetyl-7-{2-hydroxy-3-[4-(4-methoxyphenyl)-piperazinyl]propoxy}benzofuran, or the pharmaceutically acceptable acid addition salts thereof.

6. The compound of claim 2, wherein said compound is 2-acetyl-6-{2-hydroxy-3-[4-(2-methoxyphenyl)-piperazinyl]propoxy}benzofuran, or the pharmaceutically acceptable acid addition salts thereof.

7. The compound of claim 2, wherein said compound is 2-acetyl-5-{2-hydroxy-3-[4-(2-methoxyphenyl)- piperazinyl]propoxy}benzofuran, or the pharmaceutically acceptable acid addition salts thereof.

8. The compound of claim 2, wherein said compound is 2-acetyl-7-{2-hydroxy-3-[4-(2-methylphenyl)-piperazinyl]propoxy}benzofuran, or the pharmaceutically acceptable acid addition salts thereof.

9. The compound of claim 2, wherein said compound is 2-acetyl-5-{2-hydroxy-3-[4-(2-methylphenyl)-piperazinyl]-propoxy}benzofuran, or the pharmaceutically acceptable acid addition salts thereof.

10. The compound of claim 2, wherein said compound is 2-acetyl-7-{3-[4-(3-chlorophenyl)piperazinyl]-2-hydroxypropoxy}benzofuran, or the pharmaceutically acceptable acid addition salts thereof.

11. The compound or the pharmaceutically acceptable acid addition salts thereof of claim 1, wherein, in said formula (I), X is a carbamoyl group.

12. The compound of claim 11, wherein said compound is 2-carbamoyl-7-{2-hydroxy-3-[4-(2-methoxyphenyl)-piperazinyl]propoxy}benzofuran, or the pharmaceutically acceptable acid addition salts thereof.

13. The compound of claim 11, wherein said compound is 2-carbamoyl-7-{2-hydroxy-3-{4-(4-methoxyphenyl)-piperazinyl]propoxy}benzofuran, or the pharmaceutically acceptable acid addition salts thereof.

14. The compound of claim 11, wherein said compound is 2-carbamoyl-6-{2-hydroxy-3-[4-(2-methoxyphenyl)-piperazinyl]propoxy}benzofuran, or the pharmaceutically acceptable acid addition salts thereof.

15. The compound of claim 11, wherein said compound is 2-carbamoyl-5-{2-hydroxy-3-[4-(2-methoxyphenyl)-piperazinyl]propoxy}benzofuran, or the pharmaceutically acceptable acid addition salts thereof.

16. The compound of claim 11, wherein said compound is 2-carbamoyl-7-{2-hydroxy-3-[4-(2-methoxyphenyl)-piperazinyl]propoxy}benzofuran, or the pharmaceutically acceptable acid addition salts thereof.

17. The compound of claim 11, wherein said compound is 2-carbamoyl-6-{2-hydroxy-3-[4-(2-methylphenyl)-piperazinyl]propoxy}benzofuran, or the pharmaceutically acceptable acid addition salts thereof.

18. The compound of claim 11, wherein said compound is 2-carbamoyl-7-{3-[4-(3-chlorophenyl)-piperazinyl]-2-hydroxypropoxy}benzofuran, or the pharmaceutically acceptable acid addition salts thereof.

19. The compound or the pharmaceutically acceptable acid addition salts thereof of claim 1, wherein, in said formula (I), X is a cyano group.

20. The compound of claim 19, wherein said compound is 2-cyano-7-{2-hydroxy-3-[4-(2-methoxyphenyl)piperazinyl]propoxy}benzofuran, or the pharmaceutically acceptable acid addition salts thereof.

21. The compound of claim 19, wherein said compound is 2-cyano-6-{2-hydroxy-3-[4-(2-methoxyphenyl)piperazinyl]-propoxy}benzofuran, or the pharmaceutically acceptable acid addition salts thereof.

22. The compound of claim 1, wherein, in said formula (I), X is a lower alkoxycarbonyl group, or the pharmaceutically acceptable acid addition salts thereof.

23. The compound of claim 22, wherein said compound is 2-ethoxycarbonyl-7-{2-hydroxy-3-[4-(2-methoxyphenyl)-piperazinyl]propoxy}benzofuran, or the pharmaceutically acceptable acid addition salts thereof.

24. The compound of claim 22, wherein said compound is 2-ethoxycarbonyl-5-{2-hydroxy-3-[4-(2-methoxyphenyl)-piperazinyl]propoxy}benzofuran, or the pharmaceutically acceptable acid addition salts thereof.

25. The compound of claim 22, wherein said compound is 2-ethoxycarbonyl-5-{2-hydroxy-3-[4-(2-methylphenyl)piperazinyl]propoxy}benzofuran, or the pharmaceutically acceptable acid addition salts thereof.

26. The compound of claim 1, wherein in said formula (I) X is a carboxyl group, or the pharmaceutically acceptable acid addition salts thereof.

27. The compound of claim 26, wherein said compound is 2-carboxy-7-{2-hydroxy-3-[4-(2-methoxyphenyl)piperazinyl]propoxy}benzofuran, or the pharmaceutically acceptable acid addition salts thereof.

28. The compound of claim 1, wherein in said formula (I), X is 1-hydroxyethyl group, or the pharmaceutically acceptable acid addition salts thereof.

29. The compound of claim 28, wherein said compound is 2-(1-hydroxyethyl)-7-{2-hydroxy-3-[4-(2-methoxyphenyl)-piperazinyl]propoxy}benzofuran, or the pharmaceutically acceptable acid addition salts thereof.

30. The compound of claim 28, wherein said compound is 2-(1-hydroxyethyl)-7-{2-hydroxy-3-[4-(2-methylphenyl)piperazinyl]propoxy}benzofuran, or the pharmaceutically acceptable acid addition salts thereof.

31. A process for preparing a [2-hydroxy-3-(4-phenylpiperazinyl)propoxy]benzofuran compound having the formula (VI):

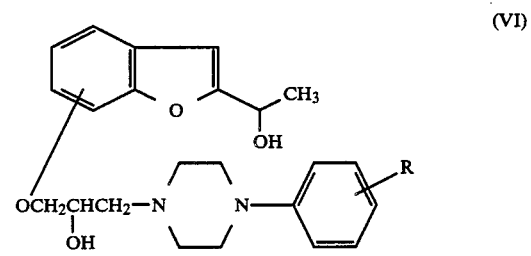

(VI)

wherein R is hydrogen atom, a lower alkoxy group, a lower alkyl group or a halogen atom; R is attached to an arbitrary position of ortho-position, meta-position and para-position to N-phenyl group, and the group having the formula:

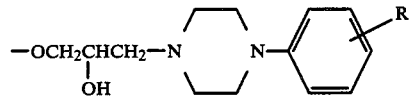

in the formula (VI) is attached to an arbitrary position of 4, 5, 6 and 7 positions to benzofuran ring, or the pharmaceutically acceptable acid addition salts thereof which comprises reducing a 2-acetylbenzofuran derivative having the formula (V):

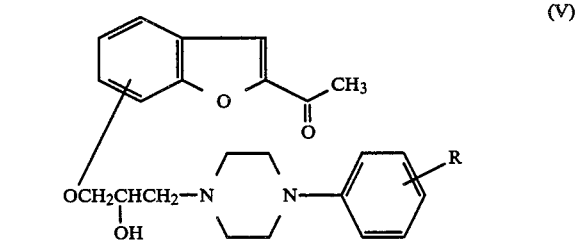

(V)

wherein R is as above.

32. A process for preparing a [2-hydroxy-3-(4-phenyl-piperazinyl)propoxy]benzofuran compound having the formula (VIII):

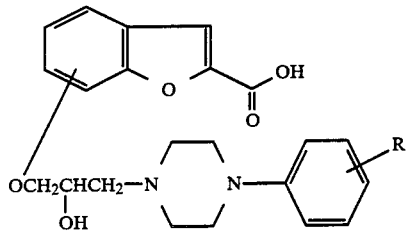
(VIII)

wherein R is hydrogen atom, a lower alkoxy group, a lower alkyl group or a halogen atom; R is attached to an arbitrary position of ortho-position, meta-position and para-position to N-phenyl group, and the group having the formula;

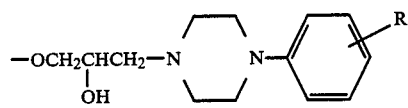

in the formula (VIII) is attached to an arbitrary position of 4, 5, 6 and 7 positions to benzofuran ring, or the pharmaceutically acceptable acid addition salts thereof which comprises reducing a benzofuran derivative having the formula (VII):

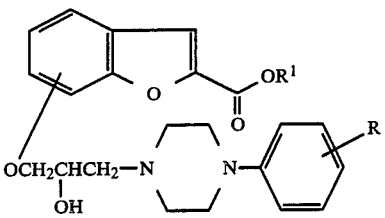
(VII)

wherein R is as above and $R^1$ is a lower alkyl group.

33. An antihypertensive agent containing a [2-hydroxy-3-(4-phenylpiperazyl)propoxy]benzofuran having the formula (I):

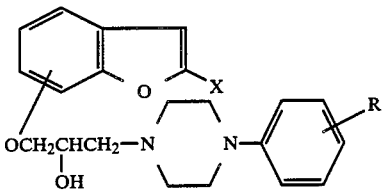
(I)

wherein X is acetyl, carbamoyl, cyano, a lower alkoxy-carbonyl, carboxyl or 1-hydroxyethyl group, R is hydrogen atom, a lower alkoxy group, a lower alkyl group or a halogen atom and is attached to an arbitrary position of ortho-position, meta-position and para-position to N-phenyl group and the group having the formula;

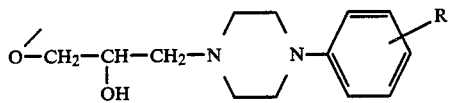

in the formula (I) is attached to an arbitrary position of 4, 5, 6 and 7 position to benzofuran ring, or the pharmaceutically acceptable acid addition salts thereof, as an effective component together with a pharmaceutically acceptable carrier.

* * * * *